United States Patent
Raisoni et al.

(10) Patent No.: US 11,666,254 B2
(45) Date of Patent: Jun. 6, 2023

(54) INTEROPERABILITY VALIDATION IN AN ANALYTE MONITORING SYSTEM

(71) Applicant: Senseonics, Incorporated, Germantown, MD (US)

(72) Inventors: Barkha Raisoni, Germantown, MD (US); Barbara Montgomery, Gaithersburg, MD (US); Suresh Addaguduru, Germantown, MD (US); Andrew DeHennis, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 90 days.

(21) Appl. No.: 16/875,577

(22) Filed: May 15, 2020

(65) Prior Publication Data
US 2020/0359944 A1 Nov. 19, 2020

Related U.S. Application Data

(60) Provisional application No. 62/849,454, filed on May 17, 2019.

(51) Int. Cl.
*A61B 5/145* (2006.01)
*A61B 5/00* (2006.01)

(52) U.S. Cl.
CPC ........ *A61B 5/14532* (2013.01); *A61B 5/0022* (2013.01); *A61B 5/7221* (2013.01);
(Continued)

(58) Field of Classification Search
CPC ........ A61B 5/0015; A61B 5/002–0024; A61B 5/0031; A61B 5/14532; A61B 5/14546;
(Continued)

(56) References Cited

U.S. PATENT DOCUMENTS 9,430,450 B1 * 8/2016 Blinn ...................... G06F 9/451
2003/0184596 A1 * 10/2003 Kodosky ................. H04L 67/36
715/810
(Continued)

FOREIGN PATENT DOCUMENTS

EP 3799395 A1 * 3/2021 .......... G06F 11/3051

OTHER PUBLICATIONS

Fodor et al. "Design Aspects of Network Assisted Device-to-Device Communications," IEEE Communications Magazine, Mar. 2012, 9 pages.

*Primary Examiner* — Navin Natnithithadha
*Assistant Examiner* — Alice Ling Zou
(74) *Attorney, Agent, or Firm* — Rothwell, Figg, Ernst & Manbeck, P.C.

(57) ABSTRACT

A system may include a first device and a second device. The second device may be configured to execute an application and validate that the application is able to cause the second device to (i) communicate with the first device and (ii) communicate with a user of the second device. The second device may be configured to (a) check one or more settings of the second device and/or (b) convey a request for data to the first device and determine whether the second device receives the requested data. The second device may be configured to cause the second device to display a message requesting confirmation that the second device displayed the message and determine whether the second device receives the requested confirmation that the second device displayed the message.

30 Claims, 14 Drawing Sheets

(52) U.S. Cl.
CPC ............ *A61B 5/742* (2013.01); *A61B 5/7405* (2013.01); *A61B 5/7455* (2013.01); *A61B 2562/02* (2013.01)

(58) Field of Classification Search
CPC ............ A61B 5/74–7405; A61B 5/742; A61B 5/7455; A61B 5/0002–0004; A61B 5/1455; A61B 5/1459; A61B 5/1468–1477; A61B 5/1486–14865; A61B 5/7221; A61B 5/7225; A61B 5/7435; A61B 5/7445; A61B 5/746–7465; A61B 2560/02; A61B 2560/0266–0276; H04L 7/0004; H04L 67/12–125; H04L 67/141; H04L 67/306; G16H 40/63–67; G16H 40/60; G06F 40/103; G06F 40/109; G06F 13/00; G05B 2219/36096
See application file for complete search history.

(56) References Cited

U.S. PATENT DOCUMENTS

| | | |
|---|---|---|
| 2005/0243619 A1 | 11/2005 | Brown et al. |
| 2007/0133567 A1 | 6/2007 | West et al. |
| 2007/0255348 A1* | 11/2007 | Holtzclaw ............... G16H 40/67 607/60 |
| 2008/0134281 A1 | 6/2008 | Shinde et al. |
| 2008/0279128 A1* | 11/2008 | Hassan ................ H04W 8/22 370/310 |
| 2008/0312584 A1* | 12/2008 | Montgomery ......... G16H 20/17 604/67 |
| 2010/0299719 A1 | 11/2010 | Burks et al. |
| 2011/0193704 A1* | 8/2011 | Harper ................ A61B 5/14 340/573.1 |
| 2011/0287528 A1* | 11/2011 | Fern ................... G16H 40/67 435/287.1 |
| 2011/0320130 A1* | 12/2011 | Valdes ................. A61B 5/7475 702/19 |
| 2012/0316412 A1 | 12/2012 | Heller et al. |
| 2013/0065517 A1* | 3/2013 | Svensson ............ H04W 12/50 455/39 |
| 2014/0012511 A1* | 1/2014 | Mensinger ........... A61B 5/7475 702/19 |
| 2014/0164544 A1 | 6/2014 | Gagneraud |
| 2015/0205947 A1* | 7/2015 | Berman ................. G16H 40/67 726/16 |
| 2016/0196676 A1* | 7/2016 | Chapman ............. G06F 40/109 345/467 |
| 2017/0132120 A1* | 5/2017 | Salameh .............. G06F 11/3616 |
| 2017/0325161 A1 | 11/2017 | Kwon et al. |
| 2018/0071913 A1* | 3/2018 | Matsudaira ............ B25J 13/006 |
| 2018/0182491 A1* | 6/2018 | Belliveau ............... G16H 80/00 |
| 2019/0132801 A1* | 5/2019 | Kamath ................. G16H 40/40 |
| 2019/0192088 A1* | 6/2019 | Raisoni ................. G16H 40/63 |
| 2019/0214150 A1* | 7/2019 | Kozloski ................ G16H 40/67 |
| 2020/0134000 A1* | 4/2020 | Liu ....................... H04L 67/02 |
| 2020/0327973 A1* | 10/2020 | Pryor .................... G16H 40/63 |

* cited by examiner

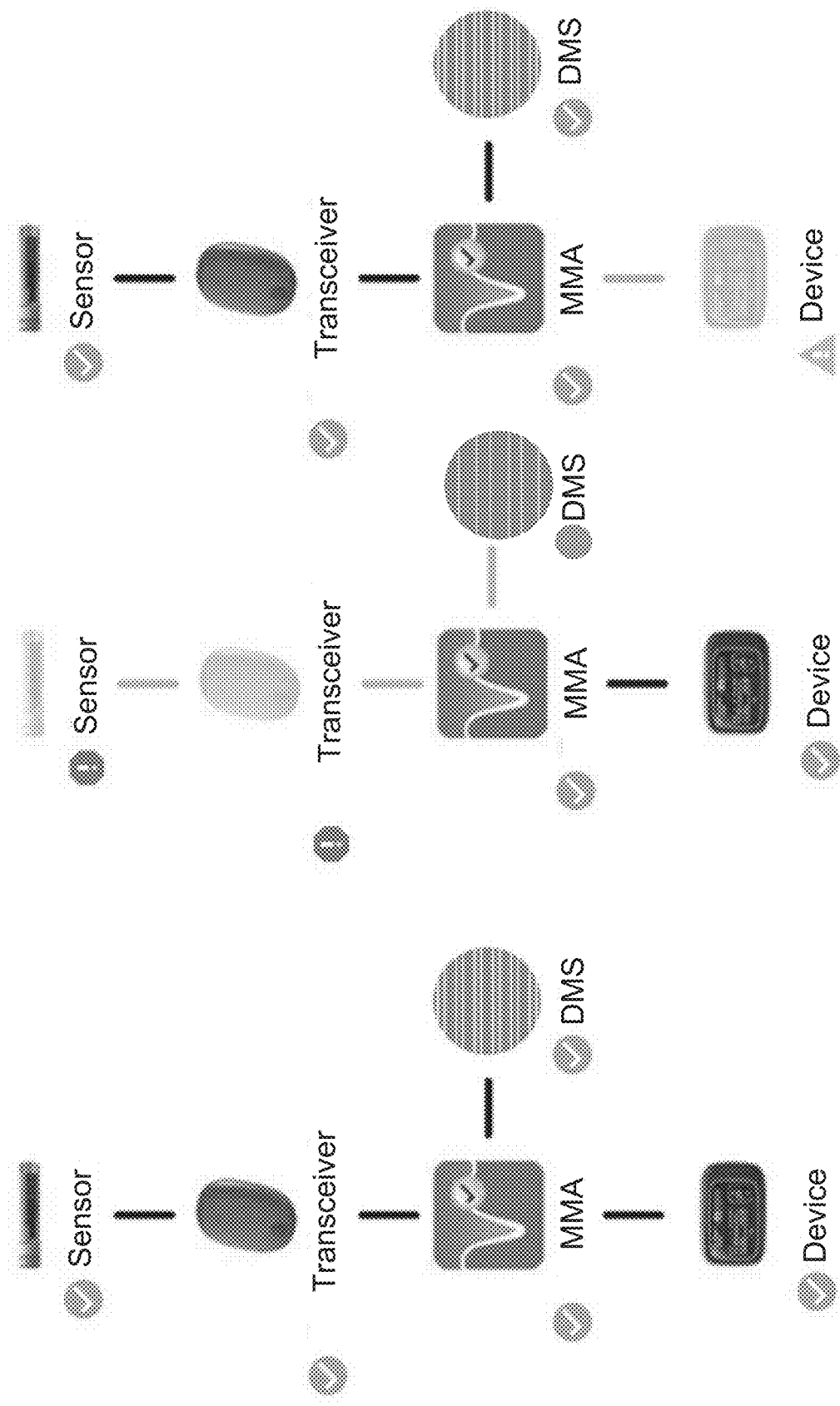

INTEROPERABILITY VALIDATION IN AN ANALYTE MONITORING SYSTEM

CROSS-REFERENCE TO RELATED APPLICATION

The present application claims the benefit of priority to U.S. Provisional Application Ser. No. 62/849,454, filed on May 17, 2019, which is incorporated herein by reference in its entirety.

BACKGROUND

Field of Invention

Aspects of the present invention relate to systems and methods for analyte monitoring. Specifically, aspects of the present invention may relate to interoperability validation in an analyte monitoring system.

Discussion of the Background

The prevalence of diabetes mellitus continues to increase in industrialized countries, and projections suggest that this figure will rise to 4.4% of the global population (366 million individuals) by the year 2030. Glycemic control is a key determinant of long-term outcomes in patients with diabetes, and poor glycemic control is associated with retinopathy, nephropathy and an increased risk of myocardial infarction, cerebrovascular accident, and peripheral vascular disease requiring limb amputation. Despite the development of new insulins and other classes of antidiabetic therapy, roughly half of all patients with diabetes do not achieve recommended target hemoglobin A1c (HbA1c) levels <7.0%.

Frequent self-monitoring of blood glucose (SMBG) is necessary to achieve tight glycemic control in patients with diabetes mellitus, particularly for those requiring insulin therapy. However, current blood (finger-stick) glucose tests are burdensome, and, even in structured clinical studies, patient adherence to the recommended frequency of SMBG decreases substantially over time. Moreover, finger-stick measurements only provide information about a single point in time and do not yield information regarding intraday fluctuations in blood glucose levels that may more closely correlate with some clinical outcomes.

Continuous glucose monitors (CGMs) have been developed in an effort to overcome the limitations of finger-stick SMBG and thereby help improve patient outcomes. These systems enable increased frequency of glucose measurements and a better characterization of dynamic glucose fluctuations, including episodes of unrealized hypoglycemia. Furthermore, integration of CGMs with automated insulin pumps allows for establishment of a closed-loop "artificial pancreas" system to more closely approximate physiologic insulin delivery and to improve adherence.

Monitoring real-time analyte measurements from a living body via wireless analyte monitoring sensor(s) may provide numerous health and research benefits. There is a need to enhance such analyte monitoring systems via innovations comprising, but not limited to, confirming the interoperability of devices in an analyte monitoring system.

SUMMARY

One aspect of the invention may provide a system including a first device and a second device. The second device may be configured to execute an application and validate that the application is able to cause the second device to (i) communicate with the first device and (ii) communicate with a user of the second device.

In some embodiments, the second device may be configured to, in validating that the application is able to cause the second device to communicate with the first device, check one or more settings of the second device. In some embodiments, the second device may be configured to, in checking the one or more settings of the second device to validate that the application is able to cause the second device to communicate with the first device, determine whether communication using a first wireless standard is enabled. In some embodiments, the first wireless standard may be a Bluetooth standard.

In some embodiments, the second device may be configured to, in validating that the application is able to cause the second device to communicate with the first device, (i) convey a request for data to the first device and (ii) determine whether the second device receives the requested data.

In some embodiments, the second device may be configured to, in validating that the application is able to cause the second device to communicate with the first device, (i) convey a command specifying an action to the first device, (ii) request confirmation that the first device performed the action specified by the command, and (iii) determine whether the second device receives the requested confirmation that the first device performed the action. In some embodiments, the command may be a display command specifying a display, and the requested confirmation is confirmation that the first device displayed the display specified by the display command. In some embodiments, the command may be a sound command specifying that the first device make a sound, and the requested confirmation is confirmation that the first device made the sound specified by the sound command. In some embodiments, the command may be a vibration command specifying that the first device vibrate, and the requested confirmation is confirmation that the first device vibrated. In some embodiments, the requested confirmation may be a user confirmation. In some embodiments, the second device may include a user input configured to receive the requested confirmation.

In some embodiments, the second device may be configured to, in validating that the application is able to cause the second device to communicate with the user of the second device, check one or more settings of the second device. In some embodiments, the second device may be configured to, in checking the one or more settings of the second device to validate that the application is able to cause the second device to communicate with the user of the second device, determine whether a current default font setting and a current default font size setting are supported by the application. In some embodiments, the second device may be configured to, in checking the one or more settings of the second device to validate that the application is able to cause the second device to communicate with the user of the second device, determine whether the second device volume is not set to off. In some embodiments, the second device may be configured to, in checking the one or more settings of the second device to validate that the application is able to cause the second device to communicate with the user of the second device, determine whether the vibration of the second device is enabled.

In some embodiments, the second device may be configured to, in validating that the application is able to cause the second device to communicate with the user of the second device, (i) cause the second device to display a message requesting confirmation that the second device displayed the message and (ii) determine whether the second device receives the requested confirmation that the second device displayed the message.

In some embodiments, the second device may include a user interface, and the second device may be configured to, in validating that the application is able to cause the second device to communicate with the user of the second device, (i) cause the user interface to perform an action, (ii) request confirmation that the user interface of the second device performed the action, and (iii) determine whether the second device receives the requested confirmation that the user interface of the second device performed the action. In some embodiments, the user interface may include a display, the action is display of a value on the display, the requested confirmation is entry of the displayed value, and determining whether the second device receives the requested confirmation may include determining whether the entered value matches the displayed value. In some embodiments, the user interface may include a speaker, the action may be making a sound, and the requested confirmation may be confirmation that the speaker made the sound. In some embodiments, the user interface may include a vibration motor, the action may be vibrating, and the requested confirmation may be confirmation that vibration motor vibrated. In some embodiments, the requested confirmation may be a user confirmation. In some embodiments, the second device may include a user input configured to receive the requested confirmation.

In some embodiments, the first device may be a transceiver configured to (i) receive measurement information from an analyte sensor, (ii) calculate an analyte level using at least the measurement information, and (iii) convey the analyte level to the second device. In some embodiments, the second device may be a display device and is configured to receive the analyte level from the transceiver and display the analyte level.

In some embodiments, the system may further include a third device, and the second device may be further configured to validate that the application is able to cause the second device to communicate with the third device. In some embodiments, the second device may be configured to, in validating that the application is able to cause the second device to communicate with the third device, check one or more settings of the second device. In some embodiments, the second device may be configured to, in checking the one or more settings of the second device to validate that the application is able to cause the second device to communicate with the third device, determine whether communication using a second wireless standard is enabled. In some embodiments, the second wireless standard may be a Wi-Fi standard. In some embodiments, the second device may be configured to, in checking the one or more settings of the second device to validate that the application is able to cause the second device to communicate with the third device, determine whether communication using one or more mobile networks is enabled. In some embodiments, the third device may be a data management system.

In some embodiments, the system may further comprise a fourth device, and the second device may be further configured to validate that the application is able to cause the second device to communicate with the fourth device. In some embodiments, the fourth device may be a wearable, analyte meter, or infusion pump.

In some embodiments, the second device may be further configured to determine whether an operating system of the second device has changed, and the second device may be configured to validate that the application is able to cause the second device to (i) communicate with the first device and (ii) communicate with a user of the second device in response to determining that the operating system of the second device has changed. In some embodiments, the second device may be further configured to determine whether one or more settings of the second device have changed, and the second device may be configured to validate that the application is able to cause the second device to (i) communicate with the first device and (ii) communicate with a user of the second device in response to determining that one or more settings of the second device have changed.

In some embodiments, the second device may be further configured to: determine whether the second device has received a notification indicating that an update to an operating system of the second device is incompatible with the application; and, in response to determining that the second device received the notification, notify a user of the second device that the update to the operating system of the second device is incompatible with the application.

In some embodiments, the second device may be configured to inform a user of a status of a connection between the first device and the second device. In some embodiments, informing the user of the connection status may include displaying a visual map including, for each device of the system, an icon corresponding to the device and an indication of whether the device is connected. In some embodiments, the icons of the visual map may be selectable, and the second device may be further configured to, in response to a selection of an icon of the visual map, provide additional information about the device to which the selected icon corresponds.

Another aspect of the invention may provide a method including executing an application on a second device. The method may include using the second device to validate that the application is able to cause the second device to (i) communicate with a first device and (ii) communicate with a user of the second device.

In some embodiments, validating that the application is able to cause the second device to communicate with the first device may include using the second device to check one or more settings of the second device. In some embodiments, checking the one or more settings of the second device to validate that the application is able to cause the second device to communicate with the first device may include using the second device to determine whether communication using a first wireless standard is enabled.

In some embodiments, validating that the application may be able to cause the second device to communicate with the first device may include using the second device to: (i) convey a request for data to the first device and (ii) determine whether the second device receives the requested data. In some embodiments, validating that the application is able to cause the second device to communicate with the first device may include using the second device to: (i) convey a command specifying an action to the first device, (ii) request confirmation that the first device performed the action specified by the command, and (iii) determine whether the second device receives the requested confirmation that the first device performed the action.

In some embodiments, validating that the application is able to cause the second device to communicate with the user of the second device may include using the second device to check one or more settings of the second device. In some embodiments, checking the one or more settings of the second device to validate that the application is able to cause the second device to communicate with the user of the second device may include one or more of: using the second device to determine whether a current default font setting and a current default font size setting are supported by the application; using the second device to determine whether the second device volume is not set to off; and using the second device to determine whether the vibration of the second device is enabled.

In some embodiments, validating that the application is able to cause the second device to communicate with the user of the second device may include using the second device to (i) cause the second device to display a message requesting confirmation that the second device displayed the message and (ii) determine whether the second device receives the requested confirmation that the second device displayed the message.

In some embodiments, validating that the application is able to cause the second device to communicate with the user of the second device may include using the second device to: (i) cause a user interface of the second device to perform an action, (ii) request confirmation that the user interface of the second device performed the action, and (iii) determine whether the second device receives the requested confirmation that the user interface of the second device performed the action. In some embodiments, the user interface may include a display, the action may be display of a value on the display, the requested confirmation may be entry of the displayed value, and determining whether the second device receives the requested confirmation ma include determining whether the entered value matches the displayed value. In some embodiments, the user interface may include a speaker, the action may be making a sound, and the requested confirmation may be confirmation that the speaker made the sound. In some embodiments, the user interface may include a vibration motor, the action may be vibrating, and the requested confirmation may be confirmation that vibration motor vibrated.

In some embodiments, the method may further include using the second device to validate that the application is able to cause the second device to communicate with a third device. In some embodiments, validating that the application is able to cause the second device to communicate with the third device may include using the second device to check one or more settings of the second device. In some embodiments, checking the one or more settings of the second device to validate that the application is able to cause the second device to communicate with the third device may include using the second device to determine whether communication using a second wireless standard is enabled.

In some embodiments, the method may further include using the second device to determine whether an operating system of the second device has changed, and validating that the application is able to cause the second device to (i) communicate with the first device and (ii) communicate with a user of the second device may occur in response to determining that the operating system of the second device has changed. In some embodiments, the method may further include using the second device to determine whether one or more settings of the second device have changed, and validating that the application is able to cause the second device to (i) communicate with the first device and (ii) communicate with a user of the second device may occur in response to determining that one or more settings of the second device have changed.

In some embodiments, the method may further include: using the second device to determine whether the second device has received a notification indicating that an update to an operating system of the second device is incompatible with the application; and, in response to determining that the second device received the notification, using the second device to notify a user of the second device that the update to the operating system of the second device is incompatible with the application.

In some embodiments, the method may further include using the second device to inform a user of a status of a connection between the first device and the second device. In some embodiments, informing the user of the connection status may include using the second device to display a visual map including, for each device of a system including at least the first and second devices, an icon corresponding to the device and an indication of whether the device is connected. In some embodiments, the icons of the visual map may be selectable, and the method may further include using the second device to, in response to a selection of an icon of the visual map, provide additional information about the device to which the selected icon corresponds.

Yet another aspect of the invention may provide a second device include a device interface, a user interface, and a computer. The device interface may be configured to communicate with a first device. The computer may include a non-transitory memory and a processor, and the computer may be configured to execute an application and validate that the application is able to cause (i) the device interface to communicate with the first device and (ii) the user interface to communicate with a user of the second device.

In some embodiments, the first device may be a transceiver configured to convey an analyte level, the device interface may be configured to receive the analyte level from the transceiver, and the application may be configured to cause the user interface to display the analyte level.

In some embodiments, the computer may be further configured to inform a user of a status of a connection between the first device and the second device. In some embodiments, informing the user of the connection status may include displaying a visual map including, for each device of a system including at least the first device and the second device, an icon corresponding to the device and an indication of whether the device is connected. In some embodiments, the icons of the visual map may be selectable, and the second device may be further configured to, in response to a selection of an icon of the visual map, provide additional information about the device to which the selected icon corresponds.

Still another aspect of the invention may provide an analyte monitoring system including an analyte sensor, a transceiver, and a display device. The transceiver may be configured to (a) receive measurement information from the analyte sensor, (b) calculate an analyte level using at least the measurement information, and (c) convey the analyte level. The display device may be configured to (a) receive the analyte level from the transceiver, (b) execute an application, and (c) validate that the application is able to cause the display device to (i) communicate with the transceiver and (ii) display the analyte level to a user of the display device.

In some embodiments, the display device may be configured to inform a user of a status of a connection between the transceiver and the display device. In some embodiments, informing the user of the connection status may include displaying a visual map including, for each of the analyte sensor, the transceiver, and the display device of the system, an icon corresponding to the device and an indication of whether the device is connected. In some embodiments, the icons of the visual map may be selectable, and the display device may be further configured to, in response to a selection of an icon of the visual map, provide additional information about the device to which the selected icon corresponds.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIGS. 14A-14D illustrate non-limiting examples of visual maps that may be displayed by a display device of an analyte monitoring system embodying aspects of the invention.

DETAILED DESCRIPTION OF PREFERRED EMBODIMENTS

Figure 1:
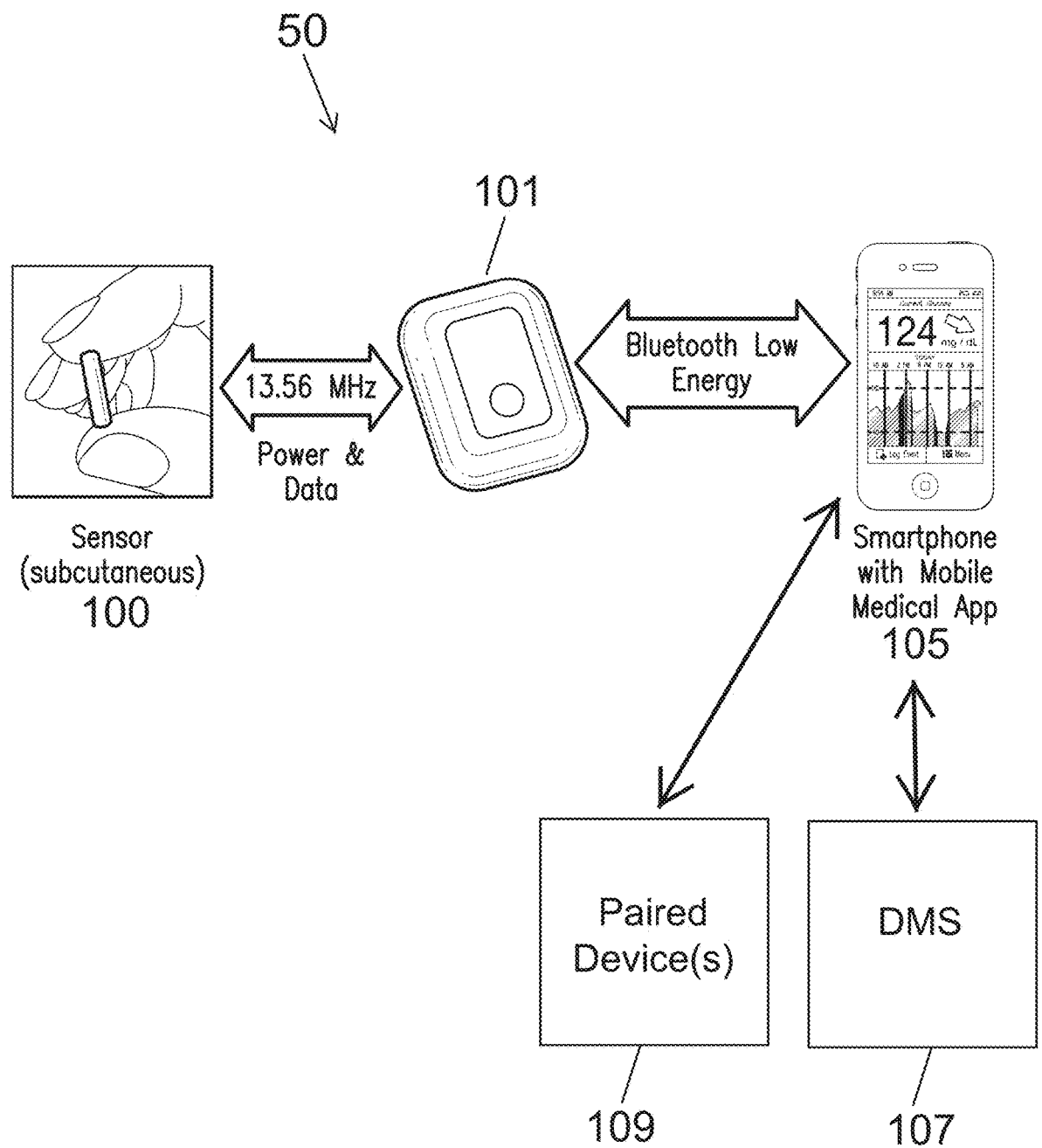
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensor 100, a transceiver 101, and a display device 105. In some embodiments, the analyte monitoring system 50 may additionally include a data management system (DMS) 107. In some embodiments, the DMS 107 may be a web-based DMS (e.g., hosted on a remote server). In some non-limiting embodiments, the DMS 107 may provide cloud storage for the analyte monitoring information of the system 50. In some embodiments, the analyte monitoring system 50 may additionally include one or more additional devices 109. In some non-limiting embodiments, the one or more additional devices 109 may include one or more wearable devices (e.g., one or more smart watches and/or one or more Fitbits), one or more infusion pumps, one or more analyte meters, and/or one or more additional devices.

In some embodiments, the sensor 100 may be small, fully subcutaneously implantable sensor. However, this is not required, and, in some alternative embodiments, the sensor 100 may be a partially implantable (e.g., transcutaneous) sensor or a fully external sensor. In some embodiments, the transceiver 101 may be an externally worn transceiver (e.g., attached via an armband, wristband, waistband, or adhesive patch). In some embodiments, the transceiver 101 may communicate with the sensor 100 to initiate and receive one or more sensor measurements via a wireless connection (e.g., via near field communication (NFC)) or a wired connection. In some embodiments, the sensor measurements may include one or more light measurements and/or one or more temperature measurements. In some embodiments, the one or more sensor measurements may be indicative of an amount or concentration of an analyte in a medium (e.g., interstitial fluid) of a living animal (e.g., a living human).

In some non-limiting embodiments, the transceiver 101 may calculate one or more analyte level (e.g., analyte concentrations) using at least the received sensor measurements. In some embodiments, the transceiver 101 may communicate information (e.g., one or more analyte levels) wirelessly (e.g., via a Bluetooth™ communication standard such as, for example and without limitation Bluetooth Low Energy) to a mobile medical application (MMA) running on a display device 105 (e.g., a smartphone or tablet). In some embodiments, the MMA may additionally or alternatively receive the information receive the information from the transceiver 101 through a wired connection (e.g., using a Universal Serial Bus (USB)) port. In some embodiments, the MMA may communicate with the data management system 107 (e.g., for plotting and sharing of the received information). In some embodiments, the MMA may additionally or alternatively communicate with one or more devices 109.

Figure 2:
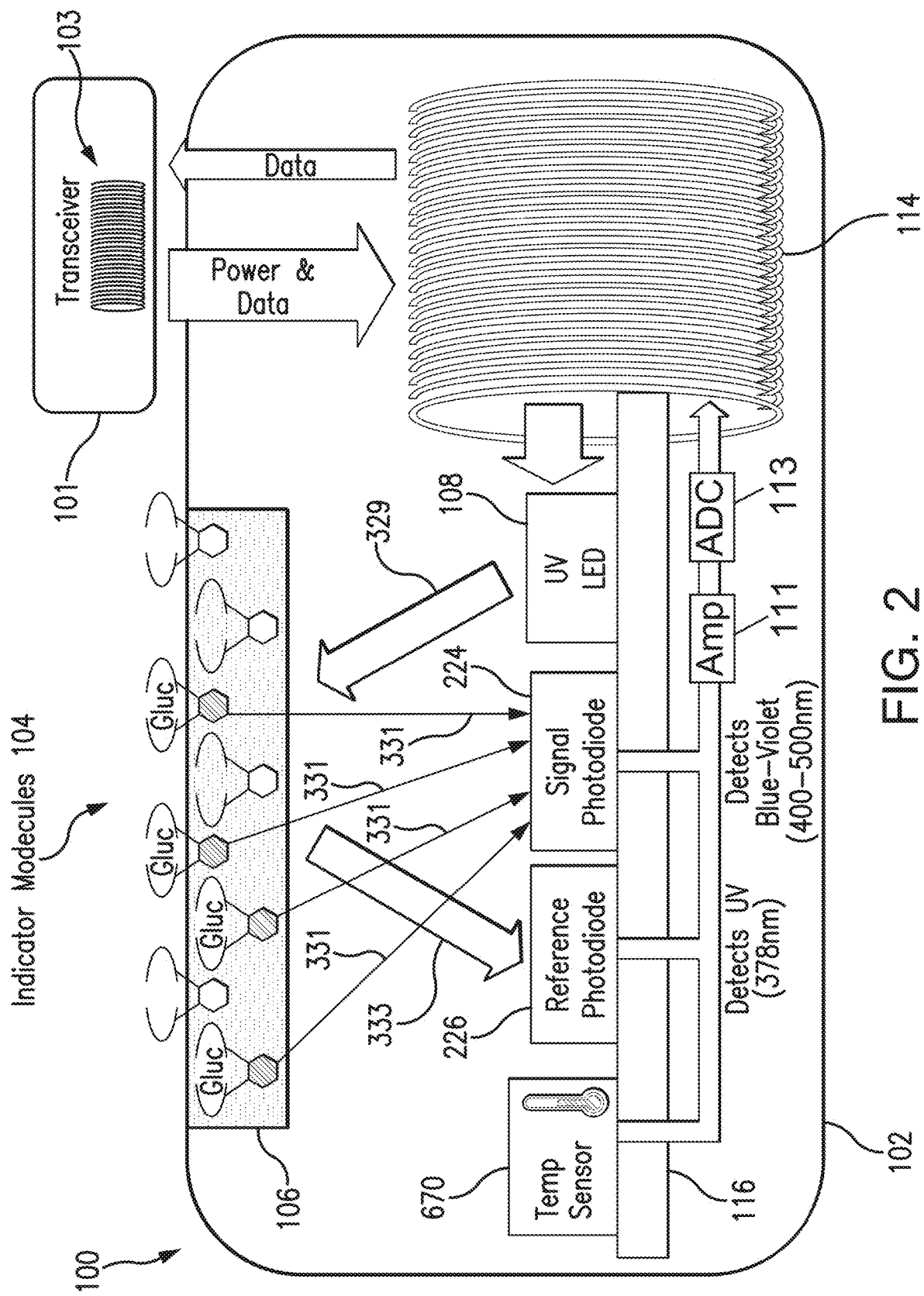
FIG. 2 is a schematic view illustrating a sensor and transceiver of an analyte monitoring system embodying aspects of the present invention.

In some embodiments, as illustrated in FIG. 2, the transceiver 101 may include an inductive element 103, such as, for example, a coil. The transceiver 101 may generate an electromagnetic wave or electrodynamic field (e.g., by using a coil) to induce a current in an inductive element 114 of the sensor 100, which powers the sensor 100. The transceiver 101 may also convey data (e.g., commands) to the sensor 100. For example, in a non-limiting embodiment, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive data (e.g., measurement information) from the sensor 100. For example, in a non-limiting embodiment, the transceiver 101 may receive data by detecting modulations in the electromagnetic wave generated by the sensor 100, e.g., by detecting modulations in the current flowing through the coil 103 of the transceiver 101.

The inductive element 103 of the transceiver 101 and the inductive element 114 of the sensor 100 may be in any configuration that permits adequate field strength to be achieved when the two inductive elements are brought within adequate physical proximity.

In some non-limiting embodiments, as illustrated in FIG. 2, the sensor 100 may be encased in a sensor housing 102 (i.e., body, shell, capsule, or encasement), which may be rigid and biocompatible. The sensor 100 may include an analyte indicator element 106, such as, for example, a polymer graft coated, diffused, adhered, or embedded on or in at least a portion of the exterior surface of the sensor housing 102. The analyte indicator element 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator element 106. In some embodiments, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator element 106 as reflection light 333. In some non-limiting embodiments, one or more of the photodetectors may be covered by one or more filters (e.g., bandpass filter 112 of FIG. 6) that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 100 may include a temperature transducer 670. In some non-limiting embodiments, the sensor 100 may include a drug-eluting polymer matrix that disperses one or more therapeutic agents (e.g., an anti-inflammatory drug).

In some embodiments, the outputs of one or more of the photodetectors 224, 226 and the temperature transducer 670 may be amplified by an amplifier 111. In some non-limiting embodiments, the amplifier 111 may be a comparator that receives analog light measurement signals from the photodetectors 224, 226 and output an analog light difference measurement signal indicative of the difference between the received analog light measurement signals. In some non-limiting embodiments, the amplifier 111 may be a transimpedance amplifier. However, in some alternative embodiments, a different amplifier may be used. In some embodiments, the outputs of one or more of the photodetectors 224, 226, the temperature transducer 670, and the amplifier 111 may be converted to a digital signal by an analog-to-digital converter (ADC) 113.

In some embodiments, as illustrated in FIG. 2, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116 and/or a core (e.g., ferrite core) for the inductive element 114. In some embodiments, the semiconductor substrate 116 and/or a core may provide communication paths between the various secured components.

In some embodiments, the one or more of the sensor housing 102, analyte indicator element 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

Although in some embodiments, as illustrated in FIG. 2, the sensor 100 may be an optical sensor, this is not required, and, in one or more alternative embodiments, sensor 100 may be a different type of analyte sensor, such as, for example, an electrochemical sensor, a diffusion sensor, or a pressure sensor. Also, although in some embodiments, as illustrated in FIGS. 1 and 2, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, the sensor 100 may include a transceiver interface device. In some embodiments where the sensor 100 includes an antenna (e.g., inductive element 114), the transceiver interface device may include the antenna (e.g., inductive element 114) of sensor 100. In some of the transcutaneous embodiments where there exists a wired connection between the sensor 100 and the transceiver 101, the transceiver interface device may include the wired connection.

Figure 3:
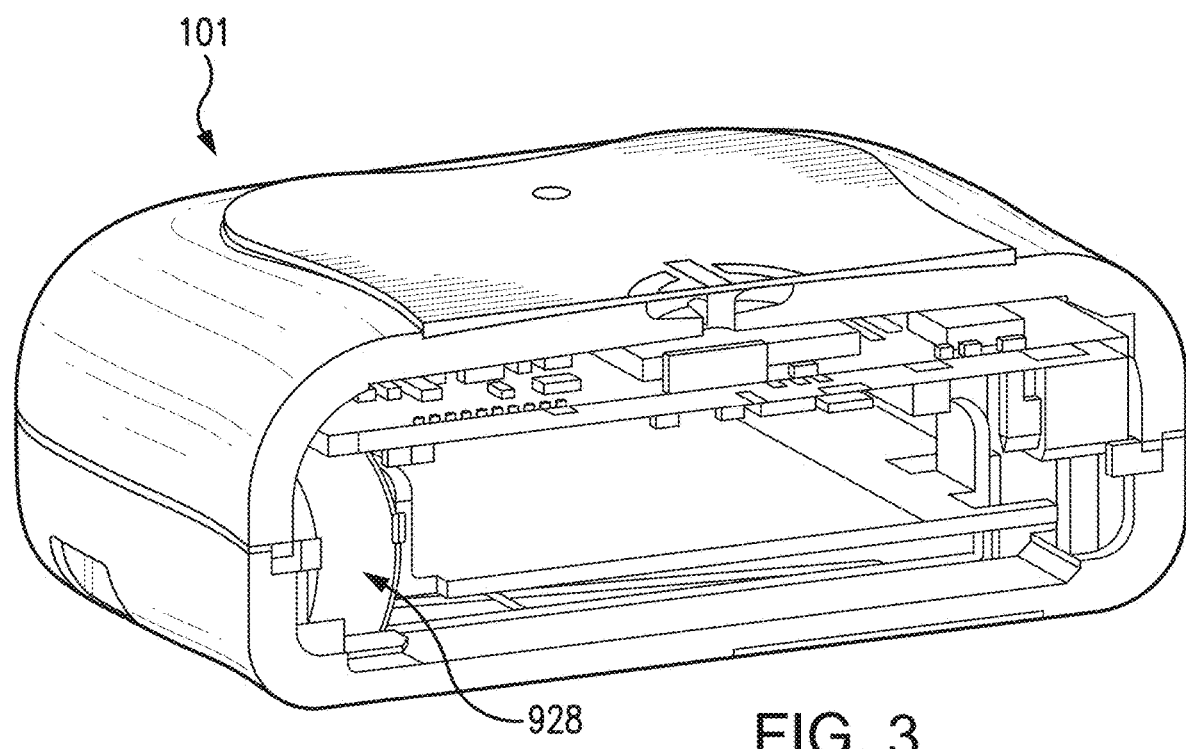
FIG. 3 is cross-sectional, perspective view of a transceiver embodying aspects of the invention.
Figure 4:
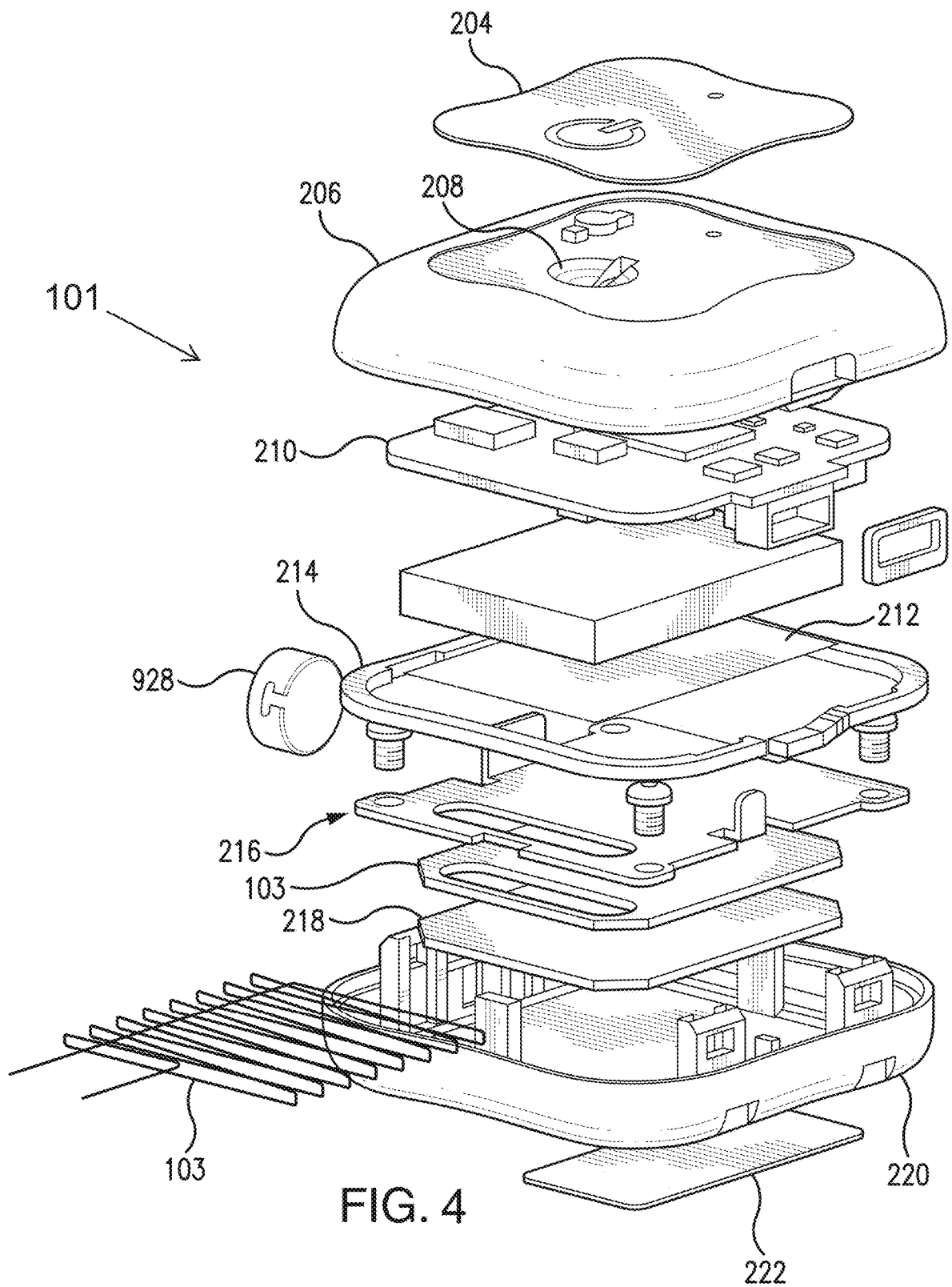
FIG. 4 is an exploded, perspective view of a transceiver embodying aspects of the invention.

FIGS. 3 and 4 are cross-sectional and exploded views, respectively, of a non-limiting embodiment of the transceiver 101, which may be included in the analyte monitoring system illustrated in FIG. 1. As illustrated in FIG. 4, in some non-limiting embodiments, the transceiver 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transceiver electronics may be assembled using standard surface mount device (SMD) reflow and solder techniques. In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transceiver assembly process may be performed at one or more electronics houses, which may be internal, external, or a combination thereof. In some embodiments, the assembled transceiver 101 may be programmed and functionally tested. In some embodiments, assembled transceivers 101 may be packaged into their final shipping containers and be ready for sale.

In some embodiments, as illustrated in FIGS. 3 and 4, the antenna 103 may be contained within the housing 206 and 220 of the transceiver 101. In some embodiments, the antenna 103 in the transceiver 101 may be small and/or flat so that the antenna 103 fits within the housing 206 and 220 of a small, lightweight transceiver 101. In some embodiments, the transceiver 101 may be suitable for placement, for example, on an abdomen area, upper-arm, wrist, or thigh of a patient body. In some non-limiting embodiments, the transceiver 101 may be suitable for attachment to a patient body by means of a biocompatible patch. Although, in some embodiments, the antenna 103 may be contained within the housing 206 and 220 of the transceiver 101, this is not required, and, in some alternative embodiments, a portion or all of the antenna 103 may be located external to the transceiver housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 5:
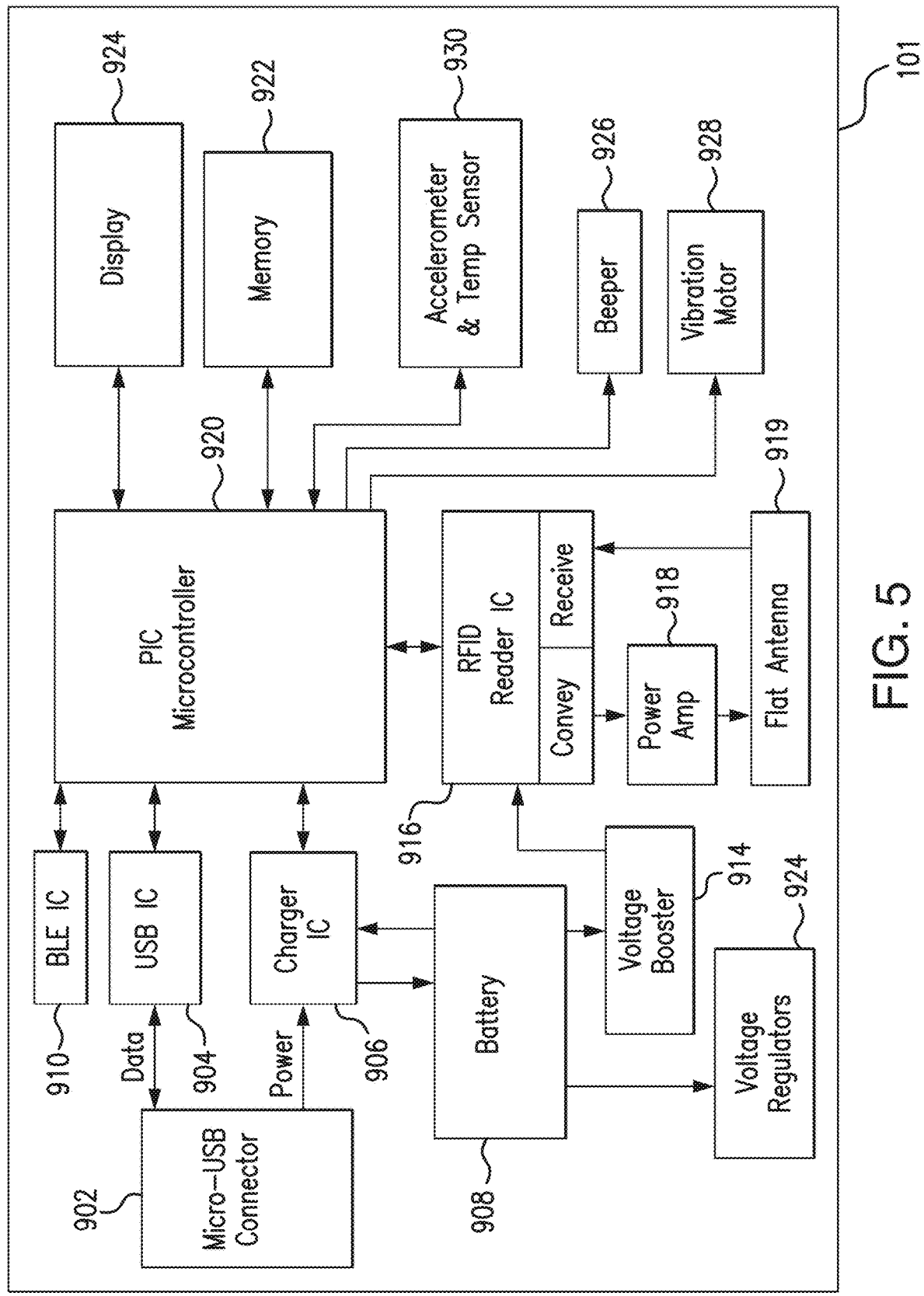
FIG. 5 is a schematic view illustrating a transceiver embodying aspects of the present invention.

FIG. 5 is a schematic view of an external transceiver 101 according to a non-limiting embodiment. In some embodiments, the transceiver 101 may have a connector 902, such as, for example, a Micro-Universal Serial Bus (USB) connector. The connector 902 may enable a wired connection to an external device, such as a personal computer or a display device 105 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer or a display device 105 (e.g., a smartphone) and/or to receive power, which may be used, for example, to charge the battery 908.

In some embodiments, the transceiver 101 may have a wireless communication IC 910, which enables wireless communication with an external device, such as, for example, one or more personal computers or one or more display devices 105 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, the transceiver 101 may include a display interface device, which may enable communication by the transceiver 101 with one or more display devices 105. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In the illustrated embodiment, the inductive element 103 is a flat antenna 919. In some non-limiting embodiments, the antenna may be flexible. However, as noted above, the inductive element 103 of the transceiver 101 may be in any configuration that permits adequate field strength to be achieved when brought within adequate physical proximity to the inductive element 114 of the sensor 100. In some embodiments, the transceiver 101 may include a power amplifier 918 to amplify the signal to be conveyed by the inductive element 103 to the sensor 100.

The transceiver 101 may include a processor 920 and a memory 922 (e.g., Flash memory). In some non-limiting embodiments, the memory 922 may be non-volatile and/or capable of being electronically erased and/or rewritten. In some non-limiting embodiments, the processor 920 may be, for example and without limitation, a peripheral interface controller (PIC) microcontroller. In some embodiments, the processor 920 may control the overall operation of the transceiver 101. For example, the processor 920 may control the connector IC 904 or wireless communication IC 910 to transmit data via wired or wireless communication and/or control the RFID reader IC 916 to convey data via the inductive element 103. The processor 920 may also control processing of data received via the inductive element 103, connector 902, or wireless communication IC 910.

In some embodiments, the transceiver 101 may include a sensor interface device, which may enable communication by the transceiver 101 with a sensor 100. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 100 and the transceiver 101 (e.g., transcutaneous embodiments), the sensor interface device may include the wired connection.

In some embodiments, the transceiver 101 may include a display 924 (e.g., liquid crystal display and/or one or more light emitting diodes), which the processor 920 may control to display data (e.g., analyte levels). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor that may be used in the processing performed by the processor 920.

In some embodiments, the transceiver 101 may be a body-worn transceiver that is a rechargeable, external device worn over the sensor implantation or insertion site. In some non-limiting embodiment, the transceiver 101 may supply power to the proximate sensor 100. In some non-limiting embodiments, power may be supplied to the sensor 100 through an inductive link (e.g., an inductive link of 13.56 MHz). However, it is not required that the sensor 100 receive power from the transceiver 101 (e.g., in the case of a battery-powered sensor). In some embodiments, the transceiver 101 may be placed using an adhesive patch or a specially designed strap or belt. The external transceiver 101 may read measured analyte data from a subcutaneous sensor 100 (e.g., up to a depth of 2 cm or more).

In some embodiments, the transceiver 100 may receive sensor data (e.g., measurement information such as, for example and without limitation, light measurements and/or temperature measurements) from the sensor 100. In some non-limiting embodiments, the transceiver 101 may periodically (e.g., every 2, 5, or 10 minutes) read sensor data. However, this is not required, and, in some alternative embodiments, the transceiver 101 may read sensor data on-demand (e.g., by swiping or bringing the transceiver 101 in proximity to the sensor 101). In some embodiments, the transceiver 101 may calculate analyte levels (e.g., analyte concentrations) using at least the received sensor data. In some embodiments, the transceiver 101 may calculate analyte level rate of change information (e.g., analyte concentration trends) using the calculated analyte levels and/or the received sensor data. In some embodiments, the transceiver 101 may transmit one or more of the calculated analyte levels and the calculated analyte level rate of change information to a display device 105 (see FIG. 1). In some embodiments, the transceiver 101 may also determine if an alert and/or alarm condition exists and generate one or more alerts or alarms, which may be signaled to the user (e.g., through vibration by vibration motor 928 and/or an LED of the transceiver's display 924 and/or a user interface of a display device 105).

In some embodiments, the transceiver 101 may convey information (e.g., one or more of sensor data, calculated analyte levels, calculated analyte level rates of change, alerts, alarms, and notifications) may be transmitted to a display device 105 (e.g., via Bluetooth Low Energy with Advanced Encryption Standard (AES)-Counter CBC-MAC (CCM) encryption) for display by a mobile medical application (MMA) being executed by the display device 105. In some non-limiting embodiments, the MMA may generate alarms, alerts, and/or notifications (in addition to or as an alternative to receiving alerts, alarms, and/or notifications from the transceiver 101). In one embodiment, the MMA may be configured to provide push notifications. In some embodiments, the transceiver 101 may have a power button (e.g., button 208) to allow the user to turn the device on or off, reset the device, or check the remaining battery life. In some embodiments, the transceiver 101 may have a button, which may be the same button as a power button or an additional button, to suppress one or more user notification signals (e.g., vibration, visual, and/or audible) of the transceiver 101 generated by the transceiver 101 in response to detection of an alert or alarm condition.

In some embodiments, the transceiver 101 of the analyte monitoring system 50 may receive raw signals indicative of an amount or concentration of an analyte in proximity to the analyte indicator element 106 of the analyte sensor 100. In some embodiments, the transceiver 101 may receive the raw signals from the sensor 100 periodically (e.g., every 5, 10, or 20 minutes). In some embodiments, the raw signals may include one or more analyte measurements (e.g., one or more measurements indicative of the level of emission light 331 from the indicator molecules 104 as measured by the photodetector 224) and/or one or more temperature measurements (e.g., as measured by the temperature transducer 670). In some embodiments, the transceiver 101 may use the received raw signals to calculate analyte levels. In some embodiments, the transceiver 100 may store one or more calculated analyte levels (e.g., in memory 922). In some embodiments, the transceiver 100 may convey one or more calculated analyte levels to the display device 105.

In some embodiments, as noted above, the transceiver 101 may calculate one or more of analyte levels and analyte level rates of change and/or may generate one or more of alerts, alarms, and notifications. However, it is not required that the transceiver 101 perform the calculations and/or generate the alerts, alarms, and notifications itself, and, in some alternative embodiments, the transceiver 101 may instead convey/relay the measurement information received from the sensor 100 to another device (e.g., display device 105) for calculation of one or more of analyte levels and analyte level rates of change and/or generation one or more of alerts, alarms, and notifications (e.g., by a mobile medical application executing on the display device 105). In some non-limiting alternative embodiments, the transceiver 101 may calculate analyte levels using at least sensor data received from the sensor 100 and convey the calculated analyte levels to the display device 105, and the display device 105 may calculate analyte level rates of change using at least the received analyte levels and/or generate one or more of alerts, alarms, and notifications using at least the received analyte levels.

Figure 6:
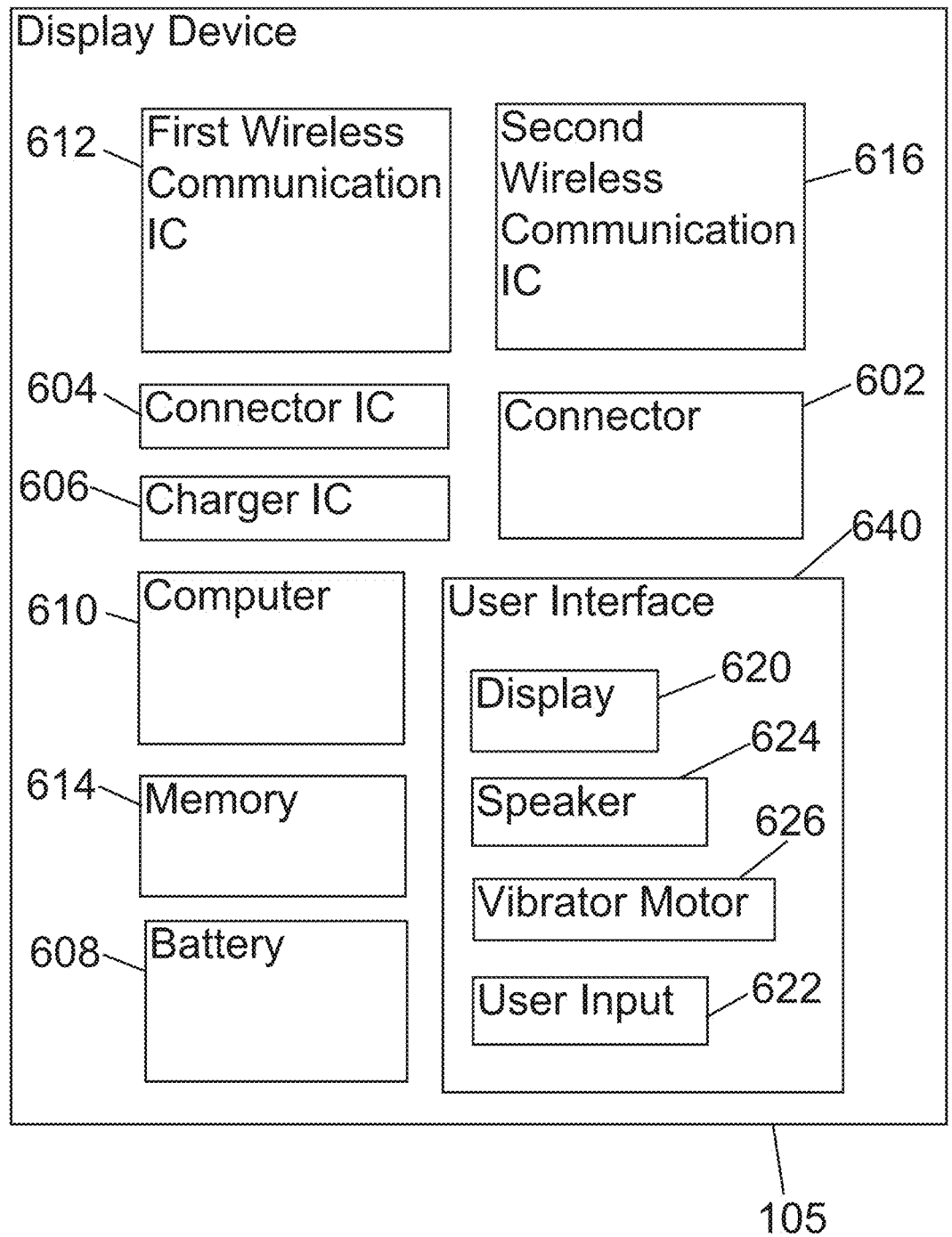
FIG. 6 illustrates a block diagram of a display device of the analyte monitoring system according to some embodiments.

FIG. 6 is a block diagram of a non-limiting embodiment of the display device 105 of the analyte monitoring system 50. As shown in FIG. 6, in some embodiments, the display device 105 may include one or more of a connector 602, a connector integrated circuit (IC) 604, a charger IC 606, a battery 608, a computer 610, a first wireless communication IC 612, a memory 614, a second wireless communication IC 616, and a user interface 640.

In some embodiments in which the display device 105 includes the connector 602, the connector 602 may be, for example and without limitation, a Micro-Universal Serial Bus (USB) connector. The connector 602 may enable a wired connection to an external device, such as a personal computer or transceiver 101 (e.g., via the connector 902 of the transceiver 101). The display device 105 may exchange data to and from the external device through the connector 602 and/or may receive power through the connector 602. In some embodiments, the connector IC 604 may be, for example and without limitation, a USB-IC, which may control transmission and receipt of data through the connector 602.

In some embodiments in which the display device 105 includes the charger IC 606, the charger IC 606 may receive power via the connector 602 and charge the battery 608. In some non-limiting embodiments, the battery 608 may be, for example and without limitation, a lithium-polymer battery. In some embodiments, the battery 608 may be rechargeable, may have a short recharge duration, and/or may have a small size.

In some embodiments, the display device 105 may include one or more connectors and/or one or more connector ICs in addition to (or as an alternative to) connector 602 and connector IC 604. For example, in some alternative embodiments, the display device 105 may include a spring-based connector (e.g., Pogo pin connector) in addition to (or as an alternative to) connector 602, and the display device 105 may use a connection established via the spring-based connector for wired communication to a personal computer or the transceiver 101 and/or to receive power, which may be used, for example, to charge the battery 608.

In some embodiments in which the display device 105 includes the first wireless communication IC 612, the first wireless communication IC 612 may enable wireless communication with one or more external devices, such as, for example, one or more personal computers, one or more transceivers 101, one or more other display devices 105, and/or one or more devices 109 (e.g., one or more wearable devices). In some non-limiting embodiments, the first wireless communication IC 612 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the first wireless communication IC 612 may be configured to wirelessly transmit data at a frequency greater than 1 gigahertz (e.g., 2.4 or 5 GHz). In some embodiments, the first wireless communication IC 612 may include an antenna (e.g., a Bluetooth antenna). In some non-limiting embodiments, the antenna of the first wireless communication IC 612 may be entirely contained within a housing of the display device 105. However, this is not required, and, in alternative embodiments, all or a portion of the antenna of the first wireless communication IC 612 may be external to the display device housing.

In some embodiments, the display device 105 may include a transceiver interface device, which may enable communication by the display device 105 with one or more transceivers 101. In some embodiments, the transceiver interface device may include the antenna of the first wireless communication IC 612 and/or the connector 602. In some non-limiting embodiments, the transceiver interface device may additionally or alternatively include the first wireless communication IC 612 and/or the connector IC 604.

In some embodiments in which the display device 105 includes the second wireless communication IC 616, the second wireless communication IC 616 may enable the display device 105 to communicate with the DMS 107 and/or one or more remote devices (e.g., smartphones, servers, and/or personal computers) via wireless local area networks (e.g., Wi-Fi), cellular networks, and/or the Internet. In some non-limiting embodiments, the second wireless communication IC 616 may employ one or more wireless communication standards to wirelessly transmit data. In some embodiments, the second wireless communication IC 616 may include one or more antennas (e.g., a Wi-Fi antenna and/or one or more cellular antennas). In some non-limiting embodiments, the one or more antennas of the second wireless communication IC 616 may be entirely contained within a housing of the display device 105. However, this is not required, and, in alternative embodiments, all or a portion of the one or more antennas of the second wireless communication IC 616 may be external to the display device housing.

In some embodiments in which the display device 105 includes the memory 614, the memory 614 may be non-volatile and/or capable of being electronically erased and/or rewritten. In some embodiments, the memory 614 may be, for example and without limitations a Flash memory.

In some embodiments in which the display device 105 includes the computer 610, the computer 610 may control the overall operation of the display device 105. For example, the computer 610 may control the connector IC 604, the first wireless communication IC 612, and/or the second wireless communication IC 616 to transmit data via wired or wireless communication. The computer 610 may additionally or alternatively control processing of received data (e.g., analyte monitoring data received from the transceiver 101).

In some embodiments in which the display device 105 includes the user interface 640, the user interface 640 may include one or more of a display 620 and a user input 622. In some embodiments, the display 620 may be a liquid crystal display (LCD) and/or light emitting diode (LED) display. In some non-limiting embodiments, the user input 622 may include one or more buttons, a keyboard, a keypad, and/or a touchscreen. In some embodiments, the computer 610 may control the display 620 to display data (e.g., analyte levels, analyte level rate of change information, alerts, alarms, and/or notifications). In some embodiments, the user interface 640 may include one or more of a speaker 624 (e.g., a beeper) and a vibration motor 626, which may be activated, for example, in the event that a condition (e.g., a hypoglycemic or hyperglycemic condition) is met.

In some embodiments, the computer 610 may execute a mobile medical application (MMA). In some embodiments, the display device 105 may receive analyte monitoring data from the transceiver 101. In some non-limiting embodiments, the received analyte monitoring data may include one or more analyte levels, one or more analyte level rates of change, and/or one or more sensor measurements. In some embodiments, the received analyte monitoring data may additionally or alternatively include alarms, alerts, and/or notifications. In some embodiments, the MMA may display some or all of the received analyte monitoring data on the display 620 of the display device 105. In some alternative embodiments, the received analyte monitoring data may include one or more sensor measurements and does not include analyte levels, and the display device 105 may calculate one or more analyte levels using the one or more sensors measurements. In some alternative embodiments, the received analyte monitoring data may include one or more analyte levels but does not include analyte level rates of change, and the display device 105 may calculate one or more analyte level rates of change using the one or more analyte levels. In some non-limiting alternative embodiments, the display device 105 may calculate one or more analyte levels and calculate one or more analyte level rates of change using at least the one or more analyte levels calculated by the display device 105.

In some embodiments, the analyte monitoring system 50 may calibrate the conversion of raw sensor measurements to analyte levels (e.g., analyte concentrations). In some embodiments, the calibration may be performed approximately periodically (e.g., every 12 or 24 hours). In some embodiments, the calibration may be performed using one or more reference measurements (e.g., one or more self-monitoring blood glucose (SMBG) measurements). In some embodiments, the reference measurements may be entered into the analyte monitoring system 50 using the user interface 640 of the display device 105. In some embodiments, the display device 105 may convey one or more references measurements to the transceiver 101, and the transceiver 101 may use the one or more received reference measurements to perform the calibration. In some alternative embodiments (e.g., embodiments in which the display device 105 calculates one or more analyte levels), the display device 105 may use the one or more received reference measurements to perform the calibration.

Figure 7:
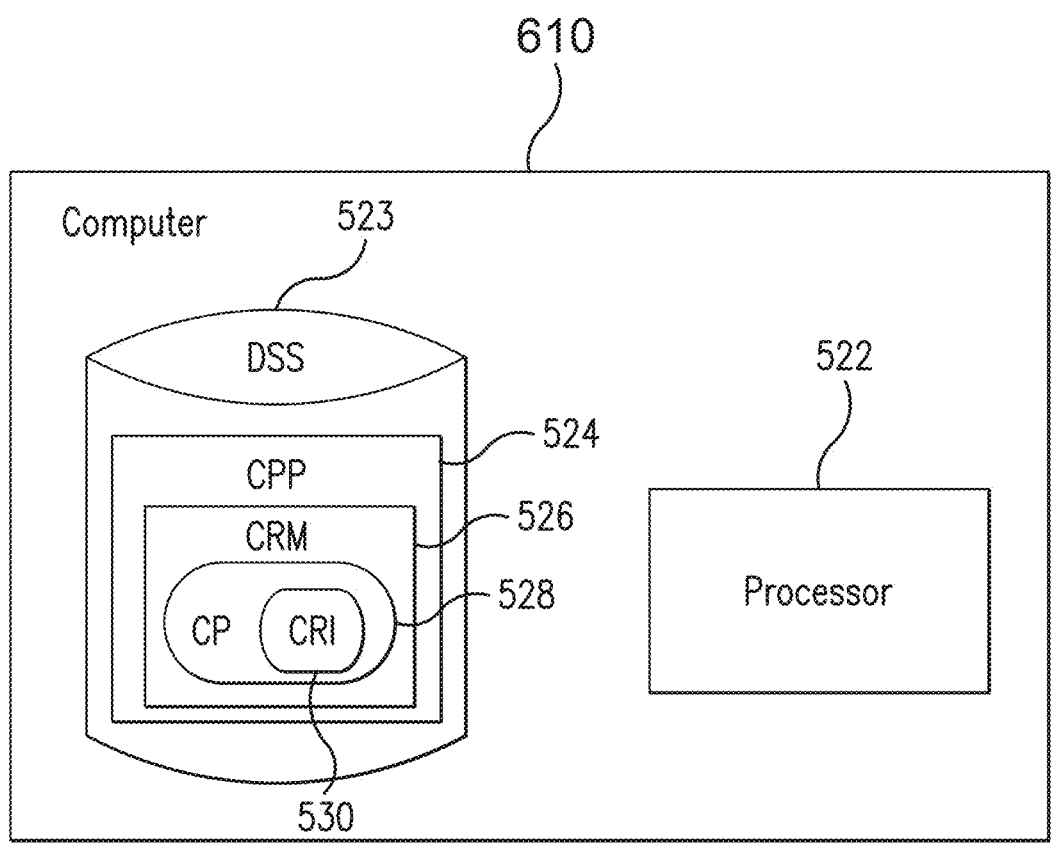
FIG. 7 illustrates a block diagram of a computer of the display device of the analyte monitoring system according to some embodiments.

FIG. 7 is a block diagram of a non-limiting embodiment of the computer 610 of the analyte monitoring system 50. As shown in FIG. 7, in some embodiments, the computer 610 may include one or more processors 522 (e.g., a general purpose microprocessor) and/or one or more circuits, such as an application specific integrated circuit (ASIC), field-programmable gate arrays (FPGAs), a logic circuit, and the like. In some embodiments, the computer 610 may include a data storage system (DSS) 523. The DSS 523 may include one or more non-volatile storage devices and/or one or more volatile storage devices (e.g., random access memory (RAM)). In embodiments where the computer 610 includes a processor 522, the DSS 523 may include a computer program product (CPP) 524. CPP 524 may include or be a computer readable medium (CRM) 526. The CRM 526 may store a computer program (CP) 528 comprising computer readable instructions (CRI) 530. In some embodiments, the CRM 526 may store, among other programs, the MMA, and the CRI 530 may include one or more instructions of the MMA. The CRM 526 may be a non-transitory computer readable medium, such as, but not limited, to magnetic media (e.g., a hard disk), optical media (e.g., a DVD), solid state devices (e.g., random access memory (RAM) or flash memory), and the like. In some embodiments, the CRI 530 of computer program 528 may be configured such that when executed by processor 522, the CRI 530 causes the computer 610 to perform steps described below (e.g., steps described below with reference to the MMA). In other embodiments, the computer 610 may be configured to perform steps described herein without the need for a computer program. That is, for example, the computer 610 may consist merely of one or more ASICs. Hence, the features of the embodiments described herein may be implemented in hardware and/or software.

In some embodiments in which the user interface 640 of the display device 105 includes the display 618, the MMA may cause the display device 105 to provide a series of graphical control elements or widgets in the user interface 640, such as a graphical user interface (GUI), shown on the display 618. The MMA may, for example without limitation, cause the display device 105 to display analyte related information in a GUI such as, but not limited to: one or more of analyte information, current analyte levels, past analyte levels, predicted analyte levels, user notifications, analyte status alerts and alarms, trend graphs, analyte level rate of change or trend arrows, and user-entered events. In some embodiments, the MMA may provide one or more graphical control elements that may allow a user to manipulate aspects of the one or more display screens. Although aspects of the MMA are illustrated and described in the context of glucose monitoring system embodiments, this is not required, and, in some alternative embodiments, the MMA may be employed in other types of analyte monitoring systems.

In some embodiments where the display device 105 communicates with a transceiver 101, which in turn obtains sensor measurement data from the analyte sensor 100, the MMA may cause the display device 105 to receive and display one or more of analyte data, trends, graphs, alarms, and alerts from the transceiver 101. In some embodiments, the MMA may store analyte level history and statistics for a patient on the display device 105 (e.g., in memory 614 and/or DSS 533) and/or in a remote data storage system.

In some embodiments, a user of the display device 105, which may be the same or different individual as patient, may initiate the download of the MMA from a central repository over a wireless cellular network or packet-switched network, such as the Internet. Different versions of the MMA may be provided to work with different commercial operating systems, such as the Android OS or Apple OS running on commercial smart phones, tablets, and the like. For example, where display device 105 is an Apple iPhone, the user may cause the display device 105 to access the Apple iTunes store to download a MMA compatible with an Apple OS, whereas where the display device 105 is an Android mobile device, the user may cause the display device 105 to access the Android App Store to download a MMA compatible with an Android OS.

Figure 8:
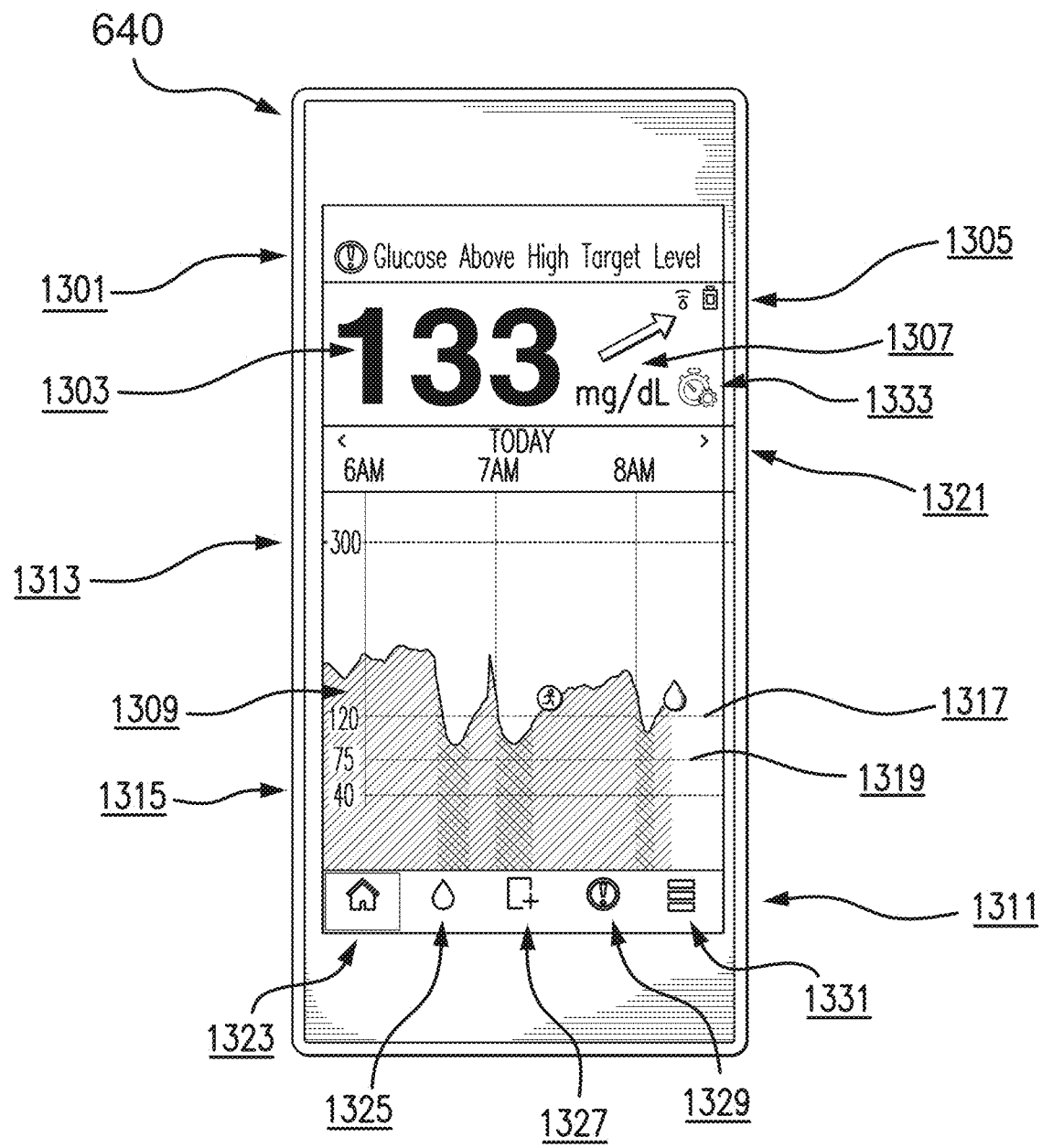
FIG. 8 illustrates a non-limiting example of a home screen illustrative display of a medical mobile application in accordance with aspects of various embodiments of the present invention.

FIG. 8 is an example of a home screen display of a medical mobile application (MMA) in accordance with aspects of various embodiments of the present invention. According to some embodiments, the workspace display of the MMA may be depicted in a GUI on the display 620 of the display device 105. In some embodiments, the home screen may display one or more of real-time analyte levels received from transceiver 101, rate and direction of analyte level change, graphical trends of analyte levels, alarms or alerts for hypoglycemia or hyperglycemia, and logged events such as, for example and without limitation, meals, exercise, and medications. In some non-limiting embodiments, the home screen may include one or more of the items or features depicted in Table 1 below.

TABLE 1

| Home Screen | |
|---|---|
| Status bar | Shows information regarding the user's analyte level and/or the system. |
| Transceiver/Transmitter ID | This is the transceiver being used; the transceiver name can be changed by going to Settings > System |
| Current analyte level | A real-time analyte level reading; this may be updated every 5 minutes |

TABLE 1-continued

| Home Screen | |
|---|---|
| Date and time | The current date and time with navigational options, such as scroll left or right to see different dates and times |
| Alarm and Events | Shows an icon when an alert, alarm, or event occurs |
| Bluetooth Connection | Shows the strength of the Bluetooth connection |
| Transmitter/Transceiver Battery Level | Indicates the battery strength of the transceiver |
| Transmitter/Transceiver Connection Status Icon | Shows the strength of the transceiver connection |
| Trend Arrow | Shows the direction a patient's analyte level is trending |
| Unit of Measurement | This is the units for the analyte level value |
| High Analyte Alarm Level | This is the high analyte alarm or alert level set by a user |
| Analyte High Target Level | This is the high analyte target level set by a user |
| Stacked Alerts | Shows when there are several alerts at the same time |
| Analyte Trend Graph | A user can navigate or scroll through the graph to see the trend over time |
| Menu | Navigation to various sections of the MMA, such as: Home   Reports   Settings Calibrate   Share My Data   About Notifications   Placement Guide Event Log   Connect |
| Calibration Point Icon | This icon appears when a calibration is entered |
| Profile Indicator | This indicator may indicate what profile is being applied, such as a normal profile, temporary profile, vacation profile, and the like. |

In some embodiments, as shown in FIG. 8, the home screen may include one or more of a status notification bar 1301, a real-time current analyte level 1303 of a patient, one or more icons 1305, a trend arrow 1307, a historical graph 1309, a profile indicator 1333, and navigation tools 1311. The status notification bar 1301 may depict, for example and without limitation, alarms, alerts, and notifications related to, for example, analyte levels and system statistics and/or status. The one or more icons 1305 may represent the signal strength of the transceiver 101 and/or the battery level of the transceiver 101. The trend arrow 1307 may indicate a rate and/or direction of change in analyte levels of a patient. The historical graph may be, for example and without limitation, a line graph and may indicate trends of analyte levels of a patient. The navigation tools 1311 may allow a user to navigate through different areas or screens of the MMA. The screens may include, for example and without limitation, one or more of Home, Calibrate, Event Log, Notifications, and Menu screens.

In some embodiments, the historical graph 1309 may depict logged events and/or user inputted activities such as meals (nutrition, amount of carbohydrates), exercise (amount of exercise), medication (amount of insulin units), and blood analyte values as icons on positions of the graph corresponding to when such events occurred. In some embodiments, the historical graph 1309 may show one or more of a boundary or indication of a high analyte alarm level 1313, a low analyte alarm level 1315, a high analyte target level 1317, and a low analyte target level 1319. In some embodiments, a user may interact with a time or date range 1321 option via the GUI to adjust the time period of the analyte level displayed on the historical graph 1309. In some embodiments, the date range 1321 may be specified by a user and may bet set to different time periods such as 1, 3, 24 hours, 1, 7, 14, 30, and 60 days, weeks, months, etc. In some embodiments, the line graph 1309 may show high, low, and average analyte levels of a patient for the selected date range 1321. In other embodiments, the line graph 1309 may be a pie chart, log book, modal day, or other depiction of analyte levels of a patient over a selectable date range 1321, any of which may further depict high, low, and average analyte levels of the patient over that date range 1321.

In some non-limiting embodiments, the trend arrow 1307 may be depicted in five different configurations that signify direction (up, down, neutral) and rate (rapidly, very rapidly slow, slow, very slow, and stable) of analyte change. In some non-limiting embodiments, the MMA and/or the transceiver 101 may use the last twenty minutes of continuous analyte measurement data received from the sensor 100 and/or calculated analyte levels in the calculation used to determine the orientation of the trend arrow 1307. In some embodiments, there may be times when the trend arrow 1307 may not be displayed due to, for example, there being insufficient sensor values available for the trend calculation. In some embodiments, a trend arrow 1307 displayed in a horizontal orientation (approximately 0° along the horizontal direction of the GUI display) may indicate that the analyte level is changing gradually, such as, for example, at a rate between −1.0 mg/dL and 1.0 mg/dL per minute. In some embodiments, a trend arrow 1307 displayed slightly in the upwards direction (approximately 45° up from the horizontal direction of the GUI display) may indicate that the analyte level is rising moderately, such as, for example, at a rate between 1.0 mg/dL and 2.0 mg/dL per minute. In some embodiments, a trend arrow 1307 displayed slightly in the downwards direction (approximately 45° down from the horizontal direction of the GUI display) may indicate that the analyte level is falling moderately, such as, for example, at a rate between 1.0 mg/dL and 2.0 mg/dL per minute. In some embodiments, a trend arrow 1307 displayed in a vertical direction (approximately 90° up from the horizontal direction of the GUI display) may indicate that the analyte level is rising very rapidly, such as, for example, at a rate more than 2.0 mg/dL per minute. In some embodiments, a trend arrow 1307 displayed in a downwards direction (approximately 90° down from the horizontal direction of the GUI display) may indicate that the analyte level is falling very rapidly, such as, for example, at a rate more than 2.0 mg/dL per minute. In some embodiments, the trend arrow 1307 is different from a predicted analyte alarm or alert. For example, the trend arrow 1307 may indicate rate and direction of change regardless of analyte value, whereas predicted analyte alarms or alerts may indicate reaching a certain analyte level based on current trends. For example, the MMA may cause a predicted low analyte alarm or alert to be displayed in the notification bar 1301 while still displaying a relatively stable trend arrow 1307 (e.g., at 0° or 45° from the horizontal direction of the GUI display).

In some embodiments, the historical line graph 1309 may allow user to quickly review and analyze historical data and/or trend information of a patient's analyte levels over time. In some embodiments, the historical line graph 1309 may include icons or markers along the trend line to reflect alarms, alerts, notifications, and/or any events that were automatically or manually logged by the user into the display device 105 via a GUI display generated by the MMA. Where one or more of such icons or markers are displayed on the historical line graph 1309, a user may select any one of the icons or markers to obtain more information about the item. For example, in response to a selection of a mark on the line graph 1309, the MMA may generate a popup window on the display 620 that provides more information about the mark.

In some embodiments, the historical line graph 1309 may enable a user to quickly review how well a patient is doing against analyte targets and/or alarms or alerts. For example, a user may establish a high analyte alarm level 1313 and/or a low analyte alarm level 1315, as well as a high analyte target level 1317 and/or a low analyte target level 1319. The high analyte alarm level 1313 and/or low analyte alarm level 1315 may be visually depicted over the historical line graph 1309, for example, using a colored dashed line (such as red). Additionally, the high analyte target level 1317 and low analyte target level 1319 may be visually depicted over the historical line graph 1309, for example, using a color dashed line (such as green).

In some embodiments, the colors of the historical line graph 1309 may change depending on an analyte level 1303 status. For example, during the times where the analyte level 1303 was outside of the high analyte alarm level 1313 or low analyte alarm level 1315, then the portion of the line graph 1309 corresponding to those times may be filled in red. As another example, during the times where the analyte level 1303 is between the high analyte target level 1317 and the low analyte target level 1319, then the portion of the line graph 1309 corresponding to those times may be filled in green. As yet another example, during the times where the analyte level 1303 is between an analyte target level 1317, 1319 and a corresponding alarm level 1313, 1315, then the portion of the line graph 1309 may be filled in yellow.

In some embodiments, the line graph 1309 may be displayed with one or more selectable date range icons 1321 that allow a user to change the day/time period corresponding to the line graph 1309 in real-time. For example, a user may select a forwards or backwards selectable option (such as an arrow) or use a swipe or fling gesture that may be recognized by GUI to navigate to a later or earlier time period, respectively, such as a day, month, etc. In some embodiments a user may choose an older graph 1309 to display by tapping the date on the date range 1321 portion of the screen and submitting or entering a desired date and/or time to review. In some embodiments, a user may use one or more gestures that are recognized by the GUI, such as a pinch, zoom, tap, press and hold, or swipe, on graph 1309. For example, a user may pinch the historical line graph 1309 with a thumb and index finger in order to cause the MMA to display different time/dating settings or adjust a time/date setting on the line graph 1309. In some embodiments, a user may tap or press and hold a time event on historical line graph 1309, and in response the MMA may display further detail on the time event, such as a history, reading value, date/time, or association to other events or display a prompt for entry of a time event.

In some embodiments, the MMA may store analyte data 1303 on the display device 105 (e.g., in memory 614 and/or DSS 533) so long as there is available memory space. Additionally or alternatively, the MMA may cause the display device 105 to send a sync request message to store the analyte data 1303 on a remote storage device.

In some embodiments, the MMA may cause the GUI to display navigational tools 1311 that allow a user to navigate to different features and screens provided by the MMA. For example, the navigational tools 1311 may comprise a navigation bar with one or more of a plurality of selectable navigation options 1323, 1325, 1327, 1329, and 1331, such as buttons or icons. As shown in FIG. 8, in some embodiments, the selectable navigation options may allow a user to navigate to one or more of the "Home" screen 1323, a "Calibrate" screen 1325, an "Event Log" screen 1327, a "Notifications" screen 1329, and a "Menu" screen 1331. Upon a user selection of one of the selectable navigation options in the navigation tools area 1311, a new screen corresponding to the selected option may be displayed on a display device by the GUI.

In some embodiments, the display device 105 may run an operating system (e.g., iOS for a display device 105 that is an Apple device or an Android operating system for a display device 105 that is an Android mobile device). In some embodiments, the operating system running on the display device 105 may change. For example, the operating system may be updated or replaced by a new version. In some embodiments, changes to the operating system running on the display device 105 may cause disruptions to the analyte monitoring system 50. That is, changes to the operating system of the display device 105 may prevent or delay the transfer of information (e.g., one or more of analyte levels, notifications, alerts, alarms) between the MMA and one or more of the transceiver 101, DMS 107, and device(s) 109. Changes to the operating system of the display device 105 may additionally or alternatively prevent or delay the analyte monitoring system 50 from providing information (e.g., one or more of analyte levels, notifications, alerts, alarms) to a user. For example, changes to the operating system of the display device 105 may cause one or more of the MMA, transceiver 101, DMS 107, and device(s) 109 to be incompatible with the display device 105. The incompatibility may be result from, for example and without limitation, the new operating system not supporting one or more features of the MMA, and/or the new operating system not being backward compatible.

In addition, changes to the settings of the display device 105 (e.g., default font settings, communication settings, and/or user interface settings) may cause one or more of the MMA, transceiver 101, DMS 107, and device(s) 109 to be incompatible with the display device 105. For example, if the user of the display device 105 has turned off the first wireless communication IC 612 (e.g., turned off Bluetooth), the display device 105 may not be able to communicate with one or more of the transceiver 101 and the device(s) 109. For another example, if the user of the display device 105 has turned off the first wireless communication IC 616 (e.g., turned off Wi-Fi and/or the connection to the Internet and/or mobile network), the display device 105 may not be able to communicate with the DMS 107. For yet another example, if the user of the display device 105 has turned off one or more of the display 620, speaker 624, and vibration motor 626 of the user interface 640, the user may not receive information (e.g., one or more of analyte levels, notifications, alerts, and alarms) from the MMA (e.g., because the user cannot hear, feel, or see notifications, alerts, and alarms).

In some embodiments, the analyte monitoring system 50 may confirm correct operation. In some embodiments, the analyte monitoring system 50 may confirm that the MMA being executed by the display device 105 is able communicate with one or more of the transceiver 101, DMS 107, and device(s) 109. In some embodiments, the analyte monitoring system 50 may additionally or alternatively confirm that the user is receiving information (e.g., one or more of analyte levels, notifications, alerts, alarms) from a user interface of one or more of the transceiver 101 and device(s) 109. In some embodiments, the analyte monitoring system 50 may confirm correct operation periodically (e.g., daily) and/or when one or more triggers occur. In some embodiments, the triggers may include one or more of a change to the operating system of the display device 105, a change to the settings of the display device 105, opening of the MMA, and a user request to confirm correct operation.

Figure 9:
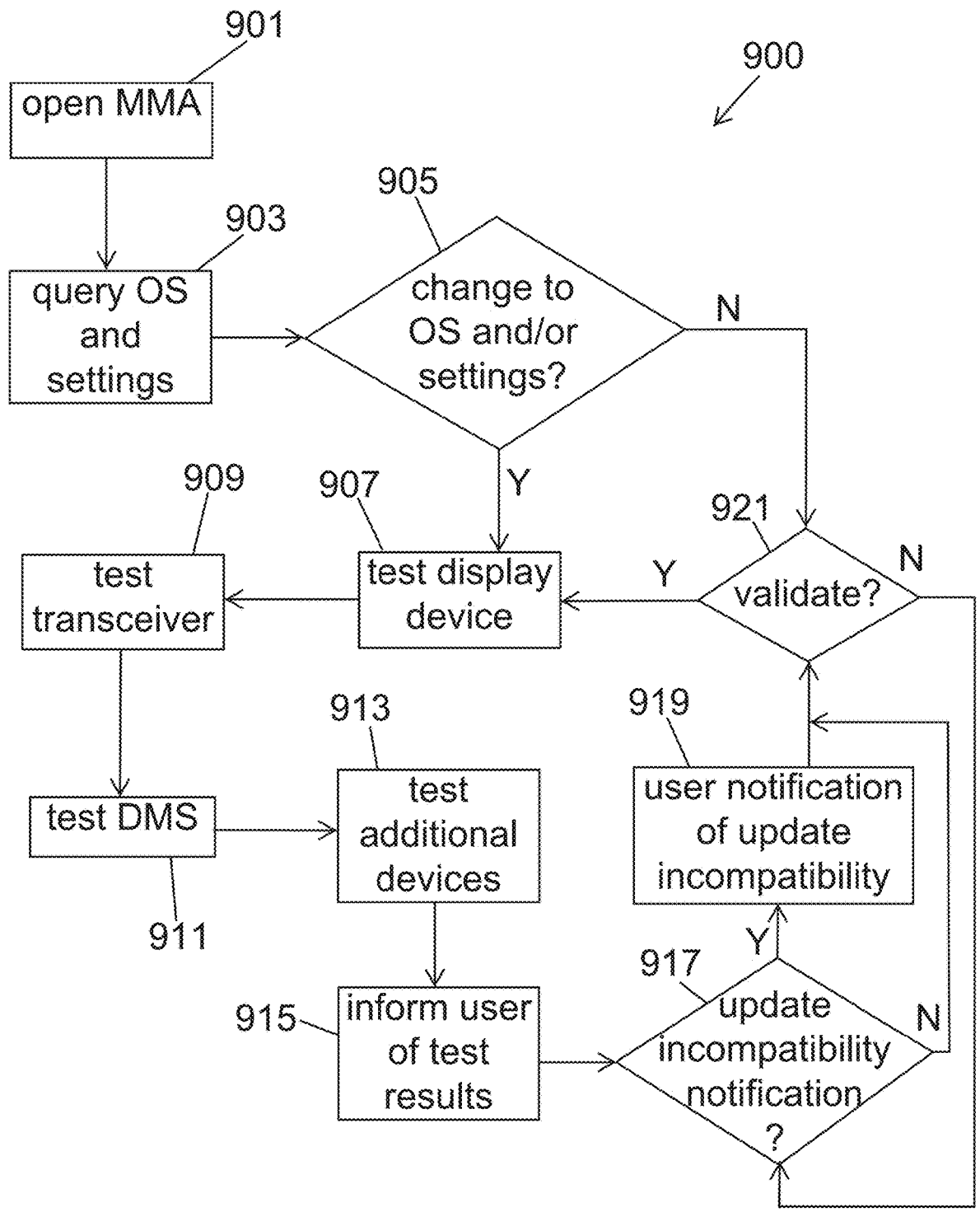
FIG. 9 is a flow chart illustrating an interoperability validation process embodying aspects of the present invention.

FIG. 9 is a flow chart illustrating an interoperability validation process 900 embodying aspects of the present invention. In some embodiments, the display device 105 may perform one or more steps of the interoperability validation process 900. In some non-limiting embodiments, the computer 610 of the display device 105 may perform one or more steps of the interoperability validation process 900. In some non-limiting embodiments, the MMA may include one or more steps of the interoperability validation process 900.

In some embodiments, the interoperability validation process 900 may include a step 901 in which the display device 105 opens the MMA (e.g., starts or begins executing the MMA). In some non-limiting embodiments, the display device 105 may perform the step 901 in response to the user of the display device 105 in response to user input received via the user input 622 of the user interface 640 of the display device 105 (e.g., in response to the user using the user input 622 to select (e.g., tap or double click) an icon for the MMA displayed on the display 620 of the user interface 640 of the display device 105).

In some embodiments, the interoperability validation process 900 may include a step 903 in which the display device 105 queries the display device 105 for information about the operating system and/or settings of the display device 105. In some embodiments, the information may be stored in a memory (e.g., memory 614 and/or DSS 533) of the display device 105. In some embodiments, the information may include, for example and without limitation, an identification of the current version and/or software of the operating system, update history, and/or an identification of when the operating system was last updated. In some embodiments, the information may additionally or alternatively include, for example and without limitation, the current settings and/or an identification of when the settings were last changed. In some embodiments, the settings may include one or more of a default font setting (e.g., Times New Roman, Courier New, Arial, or Calibri), a default font size setting (e.g., 12 point font), communication settings (e.g., one or more of Bluetooth on/off, Wi-Fi on/off, and mobile networks on/off), user interface settings (e.g., one or more of volume settings, vibration settings, display settings, and notification settings), background application settings, and alarm and/or alert threshold settings.

In some embodiments, the interoperability validation process 900 may include a step 905 in which the display device 105 determines whether the information about the operating system and/or settings of the display device 105 indicates a change to the operating system or settings. In some embodiments, if the display device 105 determines that the information indicates a change to one or more of the operating system or settings of the display device 105, the process 900 may proceed to one or more test steps (e.g., one or more of steps 907, 909, 911, and 913) to validate the correct functioning of the analyte monitoring system 50. In some embodiments, if the display device 105 determines that the information does not indicate a change to one or more of the operating system or settings of the display device 105, the process 900 may proceed to a step 921 in which the display device 105 determines whether to validate correct functioning of the analyte monitoring system 50.

In some alternative embodiments, the interoperability validation process 900 may not include steps 903 and 905, and the process 900 may proceed from the MMA being opened in step 901 to one or more test steps (e.g., one or more of steps 907, 909, 911, and 913) to validate the correct functioning of the analyte monitoring system 50 without first querying for and determining whether the operating system or settings have changed. In other words, in some alternative embodiments, the interoperability validation process 900 may perform the one or more test steps (e.g., one or more of steps 907, 909, 911, and 913) following the MMA being opened in step 901 (regardless of whether the operating system or settings have changed).

In some embodiments, the interoperability validation process 900 may include one or more test steps in which the display device 105 validates the correct functioning of the analyte monitoring system 50. In some embodiments, the one or more test steps may include a step 907 in which the display device 105 tests whether the display device 105 is functioning correctly in the analyte monitoring system 50. In some embodiments, the one or more test steps may include a step 909 in which the display device 105 tests whether the transceiver 101 is functioning correctly in the analyte monitoring system 50. In some embodiments, the one or more test steps may include a step 911 in which the display device 105 tests whether the DMS 107 is functioning correctly in the analyte monitoring system 50. In some embodiments, the one or more test steps may include a step 913 in which the display device 105 tests whether the one or more devices 109 are functioning correctly in the analyte monitoring system 50.

Figure 10:
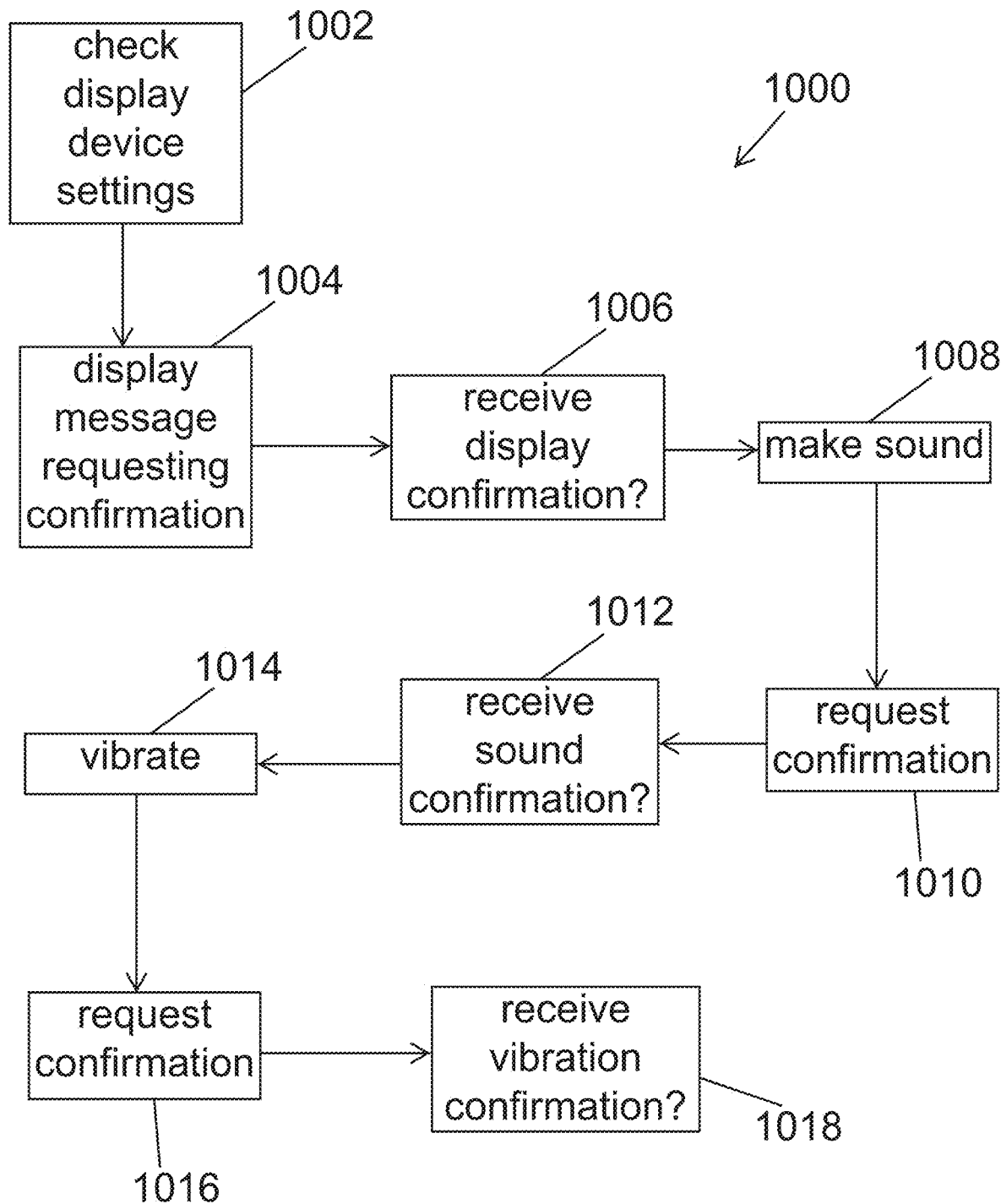
FIG. 10 is a flow chart illustrating a display device testing process embodying aspects of the present invention.

FIG. 10 is a flow chart illustrating a display device testing process 1000, which may be performed during the display device testing step 907 of the interoperability validation process 900 illustrated in FIG. 9. In some embodiments, the display device 105 may perform one or more steps of the display device testing process 1000. In some non-limiting embodiments, the computer 610 of the display device 105 may perform one or more steps of the display device testing process 1000. In some non-limiting embodiments, the MMA may include one or more steps of the display device testing process 1000.

In some embodiments, the display device testing process 1000 may include a step 1002 in which the display device 105 checks one or more settings of the display device 105. In some embodiments, checking the settings of the display device 105 may include one or more of (i) confirming that a current default font setting is set to a font supported by the MMA, (ii) confirming that a current default font size setting is set to a font size supported by the MMA, (iii) confirming that Bluetooth is turned on, (iv) confirming that Wi-Fi is turned on, (v) confirming that access to mobile networks is turned on, (vi) confirming that the display device volume is not set to off, (vii) confirming that the display device volume is not set too low, (viii) confirming that vibration is turned on, (ix) confirming that the brightness of the display 620 is not set too low, (x) confirming that notifications are enabled, (xi) confirming that background application settings will not prevent the MMA in the background from providing notifications, alerts, and/or alarms to the user, and (xii) confirming that one or more alarm and/or alert threshold settings are appropriate. In some embodiments, confirming that one or more alarm and/or alert threshold settings are appropriate may include one or more of (i) confirming that a lower analyte level alarm threshold is not set too low (e.g., not set so low that a user will be in an emergency hypoglycemic condition by the time the hypoglycemia alarm is triggered), (ii) confirming that an upper analyte level threshold is not set too high (e.g., not set so high that a user will be in an emergency hyperglycemic condition by the time the hyperglycemia alarm is triggered), (iii) confirming that a lower analyte level predictive alert threshold is not set too low (e.g., not set so low that a user may already be in an emergency hypoglycemic condition by the time the hypoglycemia predictive alert is triggered), (iv) confirming that an upper analyte level predictive alert threshold is not set too high (e.g., not set so high that a user may already be in an emergency hyperglycemic condition by the time the hyperglycemia predictive alert is triggered), and (v) confirming that an analyte level rate of change threshold is not too high (e.g., not set so high that a user's analyte level will be changing so fast that the user will not have time to take action before an emergency condition is reached).

In some embodiments, the display device testing process 1000 may include one or more steps (e.g., one or more of steps 1004, 1006, 1008, 1010, 1012, 1014, 1016, and 1018) in which the display device 105 queries the user of the display device 105 to confirm that one or more display device functions are working correctly. In some embodiments, the display device testing process 1000 may include a step 1004 in which the display device 105 displays a message (e.g., on the display 620 of the user interface 640) that requests a user action to confirm that the user saw the message (e.g., requesting user performance of a particular action such as, for example and without limitation, entry of "yes" or "okay" using the user input 622 of the user interface 640). In some embodiments, the display device testing process 1000 may include a step 1006 in which the display device 105 determines whether the display device 105 received user confirmation that the user saw the message. In some embodiments, the display device 105 may determine that the user did not see the message if the display device 105 does not receive confirmation within a threshold amount of time (e.g., 30 seconds).

In some embodiments, the step 1004 may additionally or alternative include the display device 105 displaying (e.g., on the display 620 of the user interface 640) both (i) an analyte level (e.g., an analyte level calculated by the transceiver 101 using measurement information received from the analyte sensor 100) or a code (e.g., a pseudorandom number) and (ii) a request for a user action to confirm that the user can see the analyte level or code. In some non-limiting embodiments, the requested user action to confirm that the user can see the analyte level or code may be entry of the displayed analyte level or code using the user input 622 of the user interface 640. In some embodiments, in step 1006, the display device 105 may determine that the user saw the analyte level or code if the display device 105 receives a user-entered value that matches the analyte level or code.

In some embodiments, the display device testing process 1000 may include a step 1008 in which the display device 105 makes a sound (e.g., using the speaker 624 of the user interface 640). In some embodiments, the display device testing process 1000 may include a step 1010 in which the display device 105 requests a user action to confirm that the user heard the sound (e.g., requesting user performance of a particular action such as, for example and without limitation, entry of "yes" or "okay" using the user input 622 of the user interface 640). In some embodiments, the display device testing process 1000 may include a step 1012 in which the display device 105 determines whether the display device 105 received user confirmation that the user heard the sound. In some embodiments, the display device 105 may determine that the user did not hear the sound if the display device 105 does not receive confirmation within a threshold amount of time (e.g., 30 seconds).

In some embodiments, the display device testing process 1000 may include a step 1014 in which the display device 105 vibrates (e.g., using the vibration motor 624 of the user interface 640). In some embodiments, the display device testing process 1000 may include a step 1016 in which the display device 105 requests a user action to confirm that the user felt or heard the sound (e.g., requesting user performance of a particular action such as, for example and without limitation, entry of "yes" or "okay" using the user input 622 of the user interface 640). In some embodiments, the display device testing process 1000 may include a step 1018 in which the display device 105 determines whether the display device 105 received user confirmation that the user felt or heard the vibration. In some embodiments, the display device 105 may determine that the user did not feel or hear the vibration if the display device 105 does not receive confirmation within a threshold amount of time (e.g., 30 seconds).

Figure 11:
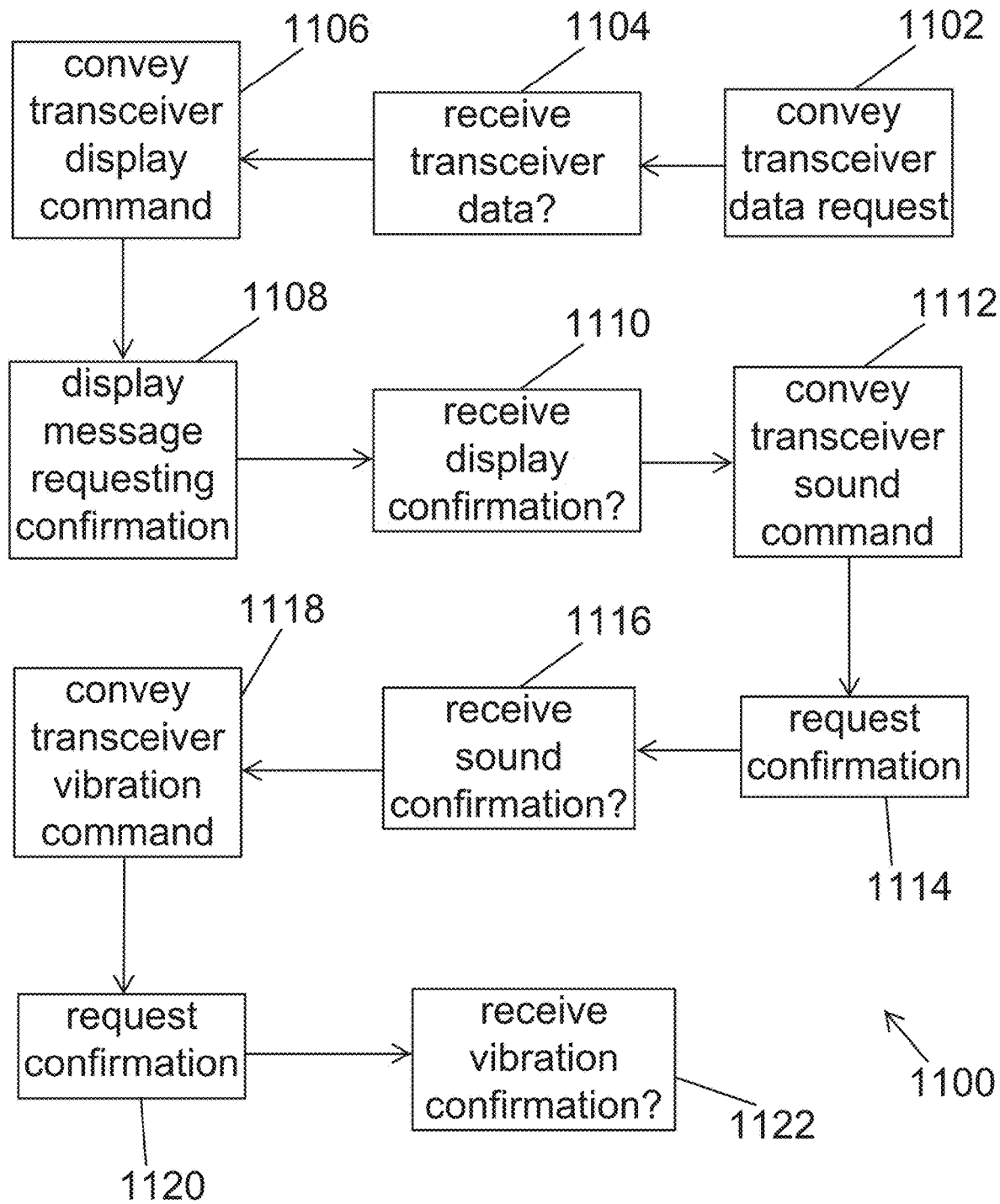
FIG. 11 is a flow chart illustrating a transceiver testing process embodying aspects of the present invention.

FIG. 11 is a flow chart illustrating a transceiver testing process 1100, which may be performed during the transceiver testing step 909 of the interoperability validation process 900 illustrated in FIG. 9, to determine whether the transceiver 101 is functioning correctly in the analyte monitoring system 50. In some embodiments, the display device 105 may perform one or more steps of the transceiver testing process 1100. In some non-limiting embodiments, the computer 610 of the display device 105 may perform one or more steps of the transceiver testing process 1100. In some non-limiting embodiments, the MMA may include one or more steps of the transceiver testing process 1100.

In some embodiments, the transceiver testing process 1100 may include a step 1102 in which the display device 105 conveys a request for data to the transceiver 101. For example, in some embodiments, in step 1102, the display device 105 may convey a request for one or more analyte levels from the transceiver 101. In some embodiments, the transceiver testing process 1100 may include a step 1104 in which the display device 105 determines whether the display device 105 received data (e.g., one or more analyte levels) from the transceiver 101. In some embodiments, the display device 105 may wait for a threshold amount of time (e.g., 1 second) before determining that the requested transceiver data was not received.

In some embodiments, the display device testing process 1000 may include one or more steps in which the display device 105 queries the user of the display device 105 to confirm that one or more transceiver functions are working correctly. In some embodiments, the transceiver testing process 1100 may include a step 1106 in which the display device 105 conveys a transceiver display command to the transceiver 101. In some non-limiting embodiments, the transceiver display command may cause transceiver 101 to make a particular display (e.g., using the display 924). For example and without limitation, the transceiver display command may cause the transceiver 101 to display a particular message on the display 924 or cause one or more LEDs of the display 924 to turn on or blink (e.g., for a particular amount of time). In some embodiments, the transceiver testing process 1100 may include a step 1108 in which the display device 105 displays a message (e.g., on the display 620 of the user interface 640 of the display device 105) that requests a user action to confirm that the user saw the transceiver display (e.g., requesting user performance of a particular action such as, for example and without limitation, entry of "yes" or "okay" using the user input 622 of the user interface 640 of the display device 105). In some embodiments, the transceiver testing process 1100 may include a step 1110 in which the display device 105 determines whether the display device 105 received user confirmation that the transceiver display occurred. In some embodiments, the display device 105 may determine that the transceiver display did not occur if the display device 105 does not receive confirmation within a threshold amount of time (e.g., 30 seconds).

In some embodiments, the transceiver testing process 1100 may include a step 1112 in which the display device 105 conveys a transceiver sound command to the transceiver 101. In some non-limiting embodiments, the transceiver sound command may cause transceiver 101 to make a particular sound (e.g., using the speaker 926). For example and without limitation, the transceiver sound command may cause the transceiver 101 to use the speaker 926 to play a particular sequence of beeps. In some embodiments, the transceiver testing process 1100 may include a step 1114 in which the display device 105 displays a message (e.g., on the display 620 of the user interface 640 of the display device 105) that requests a user action to confirm that the user heard the transceiver sound (e.g., requesting user performance of a particular action such as, for example and without limitation, entry of "yes" or "okay" using the user input 622 of the user interface 640 of the display device 105). In some embodiments, the transceiver testing process 1100 may include a step 1116 in which the display device 105 determines whether the display device 105 received user confirmation that the transceiver sound occurred. In some embodiments, the display device 105 may determine that the transceiver sound did not occur if the display device 105 does not receive confirmation within a threshold amount of time (e.g., 30 seconds).

In some embodiments, the transceiver testing process 1100 may include a step 1118 in which the display device 105 conveys a transceiver vibration command to the transceiver 101. In some non-limiting embodiments, the transceiver vibration command may cause transceiver 101 to vibrate (e.g., using the vibration motor 928). For example and without limitation, the transceiver vibrate command may cause the transceiver 101 to use the vibration motor 928 to make a particular sequence of vibrations. In some embodiments, the transceiver testing process 1100 may include a step 1120 in which the display device 105 displays a message (e.g., on the display 620 of the user interface 640 of the display device 105) that requests a user action to confirm that the user felt or heard the transceiver vibration (e.g., requesting user performance of a particular action such as, for example and without limitation, entry of "yes" or "okay" using the user input 622 of the user interface 640 of the display device 105). In some embodiments, the transceiver testing process 1100 may include a step 1122 in which the display device 105 determines whether the display device 105 received user confirmation that the transceiver vibration occurred. In some embodiments, the display device 105 may determine that the transceiver vibration did not occur if the display device 105 does not receive confirmation within a threshold amount of time (e.g., 30 seconds).

Figure 12:
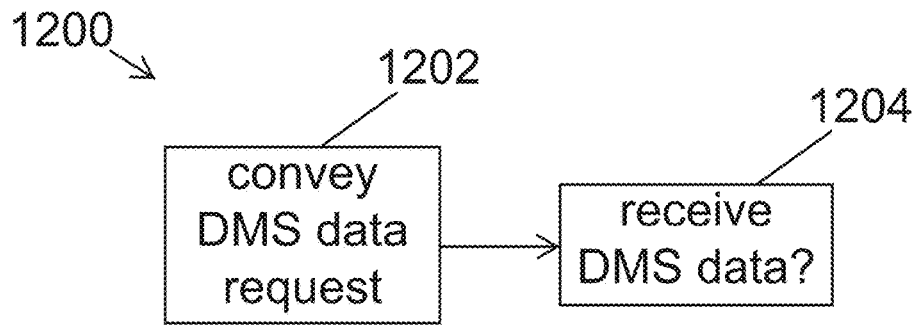
FIG. 12 is a flow chart illustrating a data management system testing process embodying aspects of the present invention.

FIG. 12 is a flow chart illustrating a DMS testing process 1200, which may be performed during the DMS testing step 911 of the interoperability validation process 900 illustrated in FIG. 9, to determine whether the DMS 107 is functioning correctly in the analyte monitoring system 50. In some embodiments, the display device 105 may perform one or more steps of the DMS testing process 1200. In some non-limiting embodiments, the computer 610 of the display device 105 may perform one or more steps of the DMS testing process 1200. In some non-limiting embodiments, the MMA may include one or more steps of the DMS testing process 1200.

In some embodiments, the DMS testing process 1200 may include a step 1202 in which the display device 105 conveys a request for data to the DMS 107. In some embodiments, the DMS testing process 1200 may include a step 1204 in which the display device 105 determines whether the display device 105 received data from the DMS 107. In some embodiments, the display device 105 may wait for a threshold amount of time (e.g., 1 second) before determining that the requested DMS data was not received.

Figure 13:
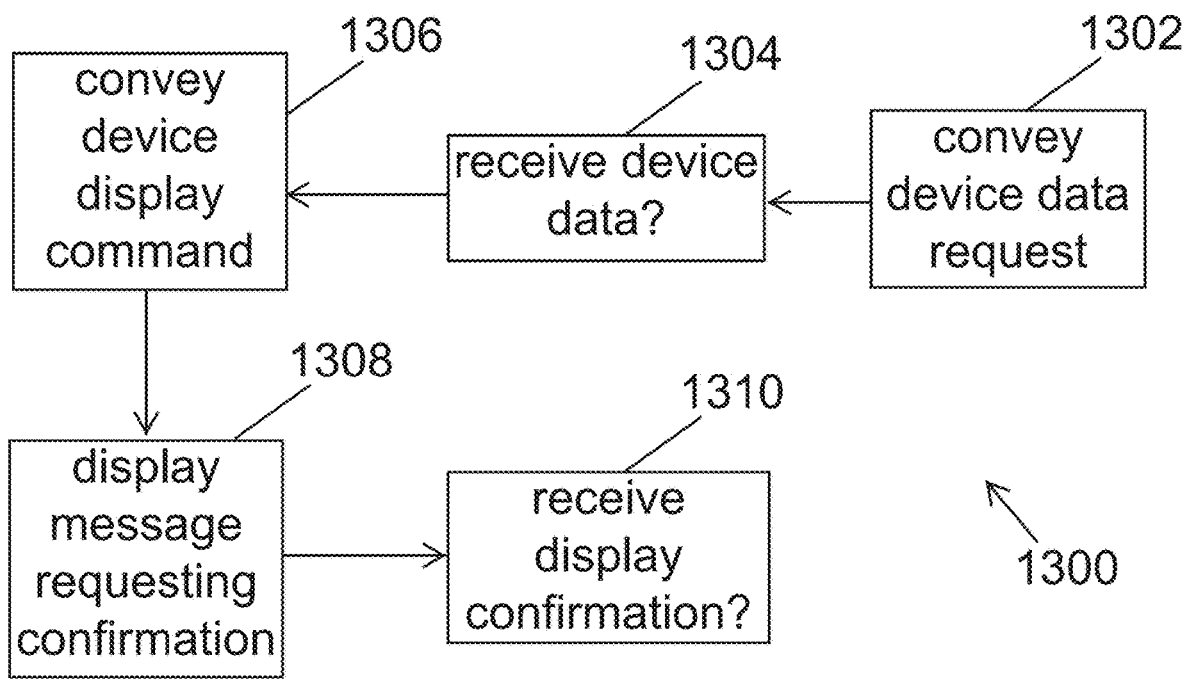
FIG. 13 is a flow chart illustrating a device testing process embodying aspects of the present invention.

FIG. 13 is a flow chart illustrating a device testing process 1300, which may be performed during the device testing step 913 of the interoperability validation process 900 illustrated in FIG. 9, to determine whether the one or more devices 109 are functioning correctly in the analyte monitoring system 50. In some embodiments, the display device 105 may perform one or more steps of the device testing process 1300. In some non-limiting embodiments, the computer 610 of the display device 105 may perform one or more steps of the device testing process 1300. In some non-limiting embodiments, the MMA may include one or more steps of the device testing process 1300.

In some embodiments, the device testing process 1300 may include a step 1302 in which the display device 105 conveys a request for data to a device 109. For example, in some embodiments where the device 109 is an analyte meter, in step 1302, the display device 105 may convey a request for one or more analyte levels from the analyte meter. For example, in some embodiments where the device 109 is a Fitbit, in step 1302, the display device 105 may convey a request for one or more activity levels and/or accelerometer information from the Fitbit. In some embodiments, the device testing process 1300 may include a step 1304 in which the display device 105 determines whether the display device 105 received data from the device 109. In some embodiments, the display device 105 may wait for a threshold amount of time (e.g., 1 second) before determining that the requested device data was not received.

In some embodiments, the device testing process 1300 may include one or more steps in which the display device 105 queries the user of the display device 105 to confirm that one or more device functions are working correctly. In some embodiments, the device testing process 1300 may include a step 1306 in which the display device 105 conveys a device display command to the device 109. In some non-limiting embodiments, the device display command may cause device 109 to make a particular display. For example and without limitation, the transceiver display command may cause the device 109 to display a particular message on the display 924 or cause one or more LEDs of the device 109 to turn on or blink (e.g., for a particular amount of time). In some embodiments, the device testing process 1300 may include a step 1408 in which the display device 105 displays a message (e.g., on the display 620 of the user interface 640 of the display device 105) that requests a user action to confirm that the user saw the device display (e.g., requesting user performance of a particular action such as, for example and without limitation, entry of "yes" or "okay" using the user input 622 of the user interface 640 of the display device 105). In some embodiments, the device testing process 1300 may include a step 1310 in which the display device 105 determines whether the display device 105 received user confirmation that the device display occurred. In some embodiments, the display device 105 may determine that the device display did not occur if the display device 105 does not receive confirmation within a threshold amount of time (e.g., 30 seconds).

In some embodiments, the device testing process 1300 may repeat one or more of steps 1302, 1304, 1306, 1308, and 1310 for each of the one or more devices 109 in the analyte monitoring system.

Figure 14D:
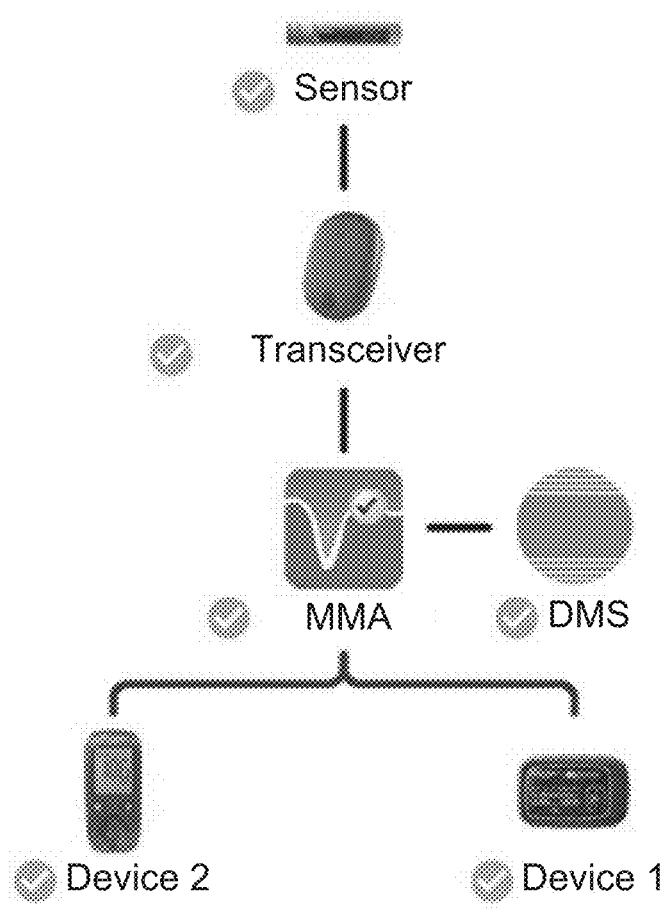

Returning to the interoperability validation process 900 illustrated in FIG. 9, in some embodiments, the interoperability validation process 900 may include a step 915 in which the display device 105 informs the user of the results of the one or more test steps (e.g., steps 907, 909, 911, and 913). In some embodiments, the display device 105 may inform the user of the one or more test results by displaying a message or graphic (e.g., the computer 610 of the display device 105 may cause the display 620 of the user interface 640 of the display device 105 to display a message or graphic). In some non-limiting embodiments, the display device 105 may inform the user of the one or more test results by displaying a graphic showing a visual map of the devices of the analyte monitoring system 50 and indications of whether the devices are connected. FIGS. 14A-14D illustrate non-limiting examples of visual maps that may be displayed by the display device 105 to indicate one or more test results. FIGS. 14A-14C illustrate a non-limiting visual map for an analyte monitoring system 50 that includes a sensor 100, a transceiver 101, a display device 105 executing an MMA, a DMS 107, and a first device 109. FIG. 14D illustrates a non-limiting example of an analyte monitoring system 50 that additionally includes a second device 109. FIGS. 14A and 14D illustrate systems in which all of the devices are connected. FIG. 14B illustrates a system in which the transceiver 101 (and sensor 100) is not connected. FIG. 14C illustrates a system in which the first device 109 is not connected.

In some embodiments, as shown in FIGS. 14A-14D, components of the analyte monitoring system 50 may be represented in the visual map by corresponding icons. For example, as shown in the FIGS. 14A-14C, the sensor 100, transceiver 101, display device 105 executing the MMA, DMS 107, and first device 109 may each be represented by a corresponding icon. As shown in FIG. 14D, the second device 109 may also be represented by corresponding icon. In some embodiments, one or more of the icons of the visual map may be selectable by the user (e.g., by using the user input 622 to select an icon of the visual map displayed on the display 620 of the user interface 640 of the display device 105). In some embodiments, a user may select an icon by tapping (or double tapping) an icon displayed on a touchscreen of the display device 105. In some embodiments, in response to receiving a user selection of an icon corresponding to a component of the analyte monitoring system 50, the display device 105 may provide additional information about the selected component (e.g., the processor 610 may cause the display 620 of the user interface 640 to display additional information about the selected component). In some non-limiting embodiments, the additional information about the selected component may include additional information about the status (e.g., connection status) of the selected component of the analyte monitoring system 50.

In some non-limiting embodiments, in step 915, the display device 105 may additionally or alternatively display a message indicating any display device setting that may interfere with proper functioning of the analyte monitoring systems. In some non-limiting embodiments, the message may indicate one or more of the following: (i) that a current default font setting is not supported by the MMA and/or that the MMA may not display messages properly, (ii) that a current default font size setting is not supported by the MMA and/or that the MMA may not display messages properly, (iii) that Bluetooth is turned off and/or that the MMA may not be able to communicate with the transceiver 101 and/or one or more devices 109, (iv) that Wi-Fi is turned off and/or that the MMA may not be able to communicate with the DMS 107, (v) that access to mobile networks is turned off and/or the MMA may not be able to communicate with the DMS 107, (vi) that the display device volume is set to off and/or that the user may not be able to hear MMA audio alerts, alarms, and notifications, (vii) that the display device volume is set too low and/or that the user may not be able to hear MMA audio alerts, alarms, and notifications, (viii) that vibration is turned off and/or that the user may not be able to feel MMA vibration alerts, alarms, and notifications, (ix) that the brightness of the display 620 is set too low and/or that the user may not be able to see the MMA display, (x) that notifications are enabled, (xi) that background application settings may prevent the MMA from providing notifications, alerts, and/or alarms to the user when the MMA is in the background, and (xii) that one or more alarm and/or alert threshold settings are inappropriate. In some non-limiting embodiments, the message may indicate one or more of the following: (i) that display device display of MMA information was not confirmed (see, e.g., steps 1004 and 1006 of FIG. 10), (ii) that display device sound was not confirmed (see, e.g., steps 1008, 1010, and 1012 of FIG. 10), (iii) that display device vibration was not confirmed (see, e.g., steps 1014, 1016, and 1018 of FIG. 10), (iv) that transceiver data transfer was not confirmed (see, e.g., steps 1102 and 1104 of FIG. 11), (v) that transceiver display was not confirmed (see, e.g., steps 1106, 1108, and 1110 of FIG. 11), (vi) that transceiver sound was not confirmed (see, e.g., steps 1112, 1114, and 1116 of FIG. 11), (vii) that transceiver vibration was not confirmed (see, e.g., steps 1118, 1120, and 1122 of FIG. 11), (viii) that DMS data transfer was not confirmed (see, e.g., steps 1202 and 1204 of FIG. 12), (ix) that device data transfer was not confirmed (see, e.g., steps 1302 and 1304 of FIG. 13), and (x) that device display was not confirmed (see, e.g., steps 1306, 1308, and 1310 of FIG. 13).

In some embodiments, the interoperability validation process 900 may include a step 917 in which the display device 105 determines whether the display device 105 has received a notification that a new version of the display device operating system is incompatible with the MMA. In some embodiments, the update incompatibility notification may be received from the DMS 107. In some embodiments, the DMS 107 may determine whether new versions of the display device operating systems and convey an update incompatibility notification to one or more display devices 105 that use the operating system. For example, in some embodiments, the DMS 107 may determine whether a new version of the operating system for Apple devices (i.e., iOS) and, if the new version is determined to be incompatible, convey an update incompatibility notification to display devices 105 that are Apple devices. Similarly, in some embodiments, the DMS 107 may determine whether a new version of the operating system for Android devices and, if the new version is determined to be incompatible, convey an update incompatibility notification to display devices 105 that are Android devices. In some non-limiting embodiments, DMS 107 may keep a list of operating system versions that are compatible with the MMA and analyte monitoring system 50 and/or a list of operating system versions that are incompatible with the MMA and analyte monitoring system 50.

In some embodiments, if the display device 105 has received an update incompatibility notification, the process 900 may proceed from step 917 to a step 919 in which display device 105 notifies the user that the new version of the display device operating system is incompatible with the MMA. In some embodiments, the display device 105 may use one or more of the display 620, speaker 624, and vibration motor 626 of the user interface 640 to notify the user. In some non-limiting embodiments, step 919 may include the display device 105 displaying a message on the display 620 warning the user that the new version of the display device operating system is incompatible with the MMA. In some non-limiting embodiments, the message may recommend that the user not update operating system. In some non-limiting embodiments, the display device 105 may require the user to confirm receipt of the user notification (e.g., by entering a response using the user input 622 of the user interface 640).

In some embodiments, the process 900 may proceed from step 919 to the step 921 in which the display device 105 determines whether to validate correct functioning of the analyte monitoring system 50. In some embodiments, if the display device 105 has not received an update incompatibility notification, the process 900 may proceed from step 917 to the step 921. In some embodiments, the analyte monitoring system 50 may determine to validate correct functioning of the analyte monitoring system 50 periodically (e.g., daily), and the display device 105 may determine to validate correct functioning if a threshold amount of time (e.g., 24 hours) has passed since correct functioning was last validated. In some embodiments, the analyte monitoring system 50 may additionally or alternatively determine to validate correct functioning of the analyte monitoring system 50 based on whether one or more triggers have occurred. In some embodiments, the triggers may include one or more of a change to the operating system of the display device 105, a change to the settings of the display device 105, and a user request to confirm correct operation (e.g., entered using the user input 622 of the user interface 640). In some embodiments, if the display device 105 determines to validate correct functioning, the process 900 may proceed from step 921 to the one or more test steps (e.g., one or more of steps 907, 909, 911, and 913). In some embodiments, if the display device 105 determines not to validate correct functioning, the process 900 may proceed from step 921 to the step 917 in which the display device 105 determines whether an update incompatibility notification has been received.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, in some non-limiting embodiments, the transceiver 101 may be a smartphone (e.g., an NFC-enabled smartphone). In some non-limiting embodiments, a smartphone (e.g., an NFC-enabled smartphone) may perform one or more functions of the transceiver 101 and the display device 105. In some non-limiting embodiments, the smartphone may take the place of both the transceiver 101 and the display device 105. That is, in some alternative embodiments, a smartphone may be used to do one or more of: (i) communicate directly with the sensor 100, (ii) power the sensor 100, (iii) calculate analyte levels using sensor data received from the sensor 100, and (iv) execute the MMA, which displays the analyte levels and/or other analyte monitoring information (e.g., analyte level rate of change or trend information, alerts, alarms, notifications). In some of these alternative embodiments, the smartphone may include the elements illustrated in FIGS. 6 and 7, and the smartphone may additionally include sensor interface elements that enable direct communication with the analyte sensor 100. In some embodiments, the sensor interface may include, for example and without limitation, one or more of an inductive element, an RFID reader IC, a power amplifier, and a voltage booster, such as those described with reference to FIG. 5 above.

For another example, although the invention is described in the context of an analyte monitoring system, the invention is applicable to other types of systems. In addition, although the invention is described in the context of a mobile medical application executed on a display device, the invention is applicable to other types of applications (e.g., non-mobile applications and/or non-medical applications) executed on other types of devices.

What is claimed is:

1. A system comprising:
   a first device;
   a second device; and
   a third device, wherein the second device is configured to:
     execute an application;
     validate that the application is able to cause the second device to (i) communicate with the first device using a first wireless standard and (ii) communicate with a user of the second device; and
     validate that the application is able to cause the second device to communicate with the third device using a second wireless standard;
   wherein the second device is configured to, in validating that the application is able to cause the second device to communicate with the third device, check one or more settings of the second device; and
   wherein the second device is configured to, in checking the one or more settings of the second device to validate that the application is able to cause the second device to communicate with the third device, determine whether communication using the second wireless standard is enabled.

2. The system of claim 1, wherein the second device is configured to, in validating that the application is able to cause the second device to communicate with the first device, check one or more settings of the second device.

3. The system of claim 2, wherein the second device is configured to, in checking the one or more settings of the second device to validate that the application is able to cause the second device to communicate with the first device, determine whether communication using the first wireless standard is enabled.

4. The system of claim 1, wherein the second device is configured to, in validating that the application is able to cause the second device to communicate with the first device, (i) convey a request for data to the first device and (ii) determine whether the second device receives the requested data.

5. The system of claim 1, wherein the second device is configured to, in validating that the application is able to cause the second device to communicate with the first device, (i) convey a command specifying an action to the first device, (ii) request confirmation that the first device performed the action specified by the command, and (iii) determine whether the second device receives the requested confirmation that the first device performed the action.

6. The system of claim 5, wherein the command is a display command specifying a display, and the requested confirmation is confirmation that the first device displayed the display specified by the display command.

7. The system of claim 5, wherein the command is a sound command specifying that the first device make a sound, and the requested confirmation is confirmation that the first device made the sound specified by the sound command.

8. The system of claim 5, wherein the command is a vibration command specifying that the first device vibrate, and the requested confirmation is confirmation that the first device vibrated.

9. The system of claim 1, wherein the second device is configured to, in validating that the application is able to cause the second device to communicate with the user of the second device, check one or more settings of the second device.

10. The system of claim 9, wherein the second device is configured to, in checking the one or more settings of the second device to validate that the application is able to cause the second device to communicate with the user of the second device, determine whether the second device volume is not set to off.

11. The system of claim 9, wherein the second device is configured to, in checking the one or more settings of the second device to validate that the application is able to cause the second device to communicate with the user of the second device, determine whether the vibration of the second device is enabled.

12. The system of claim 1, wherein the second device is configured to, in validating that the application is able to cause the second device to communicate with the user of the second device, (i) cause the second device to display a message requesting confirmation that the second device displayed the message and (ii) determine whether the second device receives the requested confirmation that the second device displayed the message.

13. The system of claim 1, wherein the second device comprises a user interface, and the second device is configured to, in validating that the application is able to cause the second device to communicate with the user of the second device, (i) cause the user interface to perform an action, (ii) request confirmation that the user interface of the second device performed the action, and (iii) determine whether the second device receives the requested confirmation that the user interface of the second device performed the action.

14. The system of claim 13, wherein the user interface comprises a display, the action is display of a value on the display, the requested confirmation is entry of the displayed value, and determining whether the second device receives the requested confirmation comprises determining whether the entered value matches the displayed value.

15. The system of claim 13, wherein the user interface comprises a speaker, the action is making a sound, and the requested confirmation is confirmation that the speaker made the sound.

16. The system of claim 13, wherein the user interface comprises a vibration motor, the action is vibrating, and the requested confirmation is confirmation that vibration motor vibrated.

17. The system of claim 1, wherein the first device is a transceiver configured to (i) receive measurement information from an analyte sensor, (ii) calculate an analyte level using at least the measurement information, and (iii) convey the analyte level to the second device.

18. The system of claim 17, wherein the second device is a display device and is configured to receive the analyte level from the transceiver and display the analyte level.

19. The system of claim 1, wherein the second device is configured to, in checking the one or more settings of the second device to validate that the application is able to cause the second device to communicate with the third device, determine whether communication using one or more mobile networks is enabled.

20. The system of claim 1, wherein the second device is further configured to determine whether an operating system of the second device has changed, and the second device is configured to validate that the application is able to cause the second device to (i) communicate with the first device and (ii) communicate with a user of the second device in response to determining that the operating system of the second device has changed.

21. The system of claim 1, wherein the second device is further configured to determine whether one or more settings of the second device have changed, and the second device is configured to validate that the application is able to cause the second device to (i) communicate with the first device and (ii) communicate with a user of the second device in response to determining that one or more settings of the second device have changed.

22. The system of claim 1, wherein the second device is further configured to:
determine whether the second device has received a notification indicating that an update to an operating system of the second device is incompatible with the application; and
in response to determining that the second device received the notification, notify a user of the second device that the update to the operating system of the second device is incompatible with the application.

23. The system of claim 1, wherein the second device is further configured to inform a user of a status of a connection between the first device and the second device.

24. The system of claim 23, wherein informing the user of the connection status comprises displaying a visual map including, for each device of the system, an icon corresponding to the device and an indication of whether the device is connected.

25. The system of claim 24, wherein the icons of the visual map are selectable, and the second device is further configured to, in response to a selection of an icon of the visual map, provide additional information about the device to which the selected icon corresponds.

26. The system of claim 1, wherein the first wireless standard is a Bluetooth standard, and the second wireless standard is a Wi-Fi standard.

27. A system comprising:
a first device; and
a second device configured to execute an application and validate that the application is able to cause the second device to (i) communicate with the first device and (ii) communicate with a user of the second device;
wherein the second device is configured to, in validating that the application is able to cause the second device to communicate with the user of the second device, check one or more settings of the second device;
wherein the second device is configured to, in checking the one or more settings of the second device to validate that the application is able to cause the second device to communicate with the user of the second device, determine whether a current default font setting and a current default font size setting are supported by the application.

28. A method comprising:
executing an application on a second device;
using the second device to validate that the application is able to cause the second device to (i) communicate with a first device using a first wireless standard and (ii) communicate with a user of the second device; and
using the second device to validate that the application is able to cause the second device to communicate with a third device using a second wireless standard;
wherein validating that the application is able to cause the second device to communicate with the third device comprises checking one or more settings of the second device; and
wherein checking the one or more settings of the second device to validate that the application is able to cause the second device to communicate with the third device comprises determining whether communication using the second wireless standard is enabled.

29. The method of claim 28, wherein the first wireless standard is a Bluetooth standard, and the second wireless standard is a Wi-Fi standard.

30. A method comprising:
executing an application on a second device; and
using the second device to validate that the application is able to cause the second device to (i) communicate with a first device and (ii) communicate with a user of the second device;
wherein validating that the application is able to cause the second device to communicate with the user of the second device comprises checking one or more settings of the second device;
wherein checking the one or more settings of the second device to validate that the application is able to cause the second device to communicate with the user of the second device comprises determining whether a current default font setting and a current default font size setting are supported by the application.

\* \* \* \* \*